US005611900A

United States Patent [19]
Worden et al.

[11] Patent Number: 5,611,900
[45] Date of Patent: Mar. 18, 1997

[54] MICROBIOSENSOR USED IN-SITU

[75] Inventors: R. Mark Worden, Holt, Mich.; David Emerson; Serban F. Peteu, both of East Lansing, all of Mich.

[73] Assignee: Michigan State University, East Lansing, Mich.

[21] Appl. No.: 504,687

[22] Filed: Jul. 20, 1995

[51] Int. Cl.$^6$ .................................................. G01N 27/26
[52] U.S. Cl. ........................ 204/403; 204/415; 204/435; 435/817; 435/287.9; 435/287.5
[58] Field of Search .................................. 204/403, 415, 204/435; 435/288, 291, 817

[56] References Cited

U.S. PATENT DOCUMENTS

| | | | |
|---|---|---|---|
| 4,671,288 | 6/1987 | Gough | 204/415 |
| 4,680,268 | 7/1987 | Clark, Jr. | 435/291 |
| 4,808,292 | 2/1989 | Kessler et al. | 204/403 |
| 4,816,131 | 3/1989 | Bomsztyk | 204/403 |
| 4,871,440 | 10/1989 | Nagata et al. | 204/403 |
| 5,007,424 | 4/1991 | Ahsbahs et al. | 204/403 |
| 5,037,527 | 8/1991 | Hayashi et al. | 204/403 |
| 5,089,112 | 2/1992 | Skothein et al. | 204/403 |
| 5,120,420 | 6/1992 | Nankai et al. | 204/403 |
| 5,147,781 | 9/1992 | Rishpon et al. | 435/7.4 |
| 5,171,689 | 12/1992 | Kawaguri et al. | 435/290 |
| 5,177,012 | 1/1993 | Kim et al. | 435/175 |
| 5,185,256 | 2/1993 | Nankai et al. | 435/174 |
| 5,186,808 | 2/1993 | Yamaguchi et al. | 204/418 |
| 5,192,507 | 3/1993 | Taylor et al. | 422/68.1 |
| 5,223,123 | 6/1993 | Koch | 204/415 |
| 5,223,124 | 6/1993 | Ege | 204/418 |
| 5,225,064 | 7/1993 | Henkens et al. | 204/403 |
| 5,236,570 | 8/1993 | Ma et al. | 2094/403 |
| 5,286,364 | 2/1994 | Yacynych et al. | 204/418 |
| 5,288,613 | 2/1994 | Luong et al. | 435/25 |
| 5,288,636 | 2/1994 | Pollmann et al. | 435/288 |
| 5,322,609 | 6/1994 | Graham | 204/403 |
| 5,334,296 | 8/1994 | Henkens et al. | 204/153.12 |
| 5,356,786 | 10/1994 | Heller et al. | 435/14 |
| 5,431,160 | 7/1995 | Wilkins | 204/415 |

FOREIGN PATENT DOCUMENTS

WO9204438  3/1992  WIPO.
WO9212413  7/1992  WIPO.

OTHER PUBLICATIONS

"Food Allergies", in Food Safety Assessment, ACS Symposium Series, Taylor S.L. et al. (1992) 484, Maple Press, New York, PA, Chapter 28 no month available.

Bulletin of Environmental contamination and Toxicology, Trevors J.T., and Basaraba J. (1980), 25(4): 672 no month available.

Polyurethanes in Biomedical Engineering II, Proceedings of the 2nd International Conference on Polyurethanes in Biomedical Engineering, Fellbach/Stuttgart, Jun. 18–19, 1986, ed. H. Planck et al.

(List continued on next page.)

Primary Examiner—Bruce F. Bell
Attorney, Agent, or Firm—Reising, Ethington, Barnard & Perry

[57] ABSTRACT

The present invention is a novel, ultra-small tip, internal referenced, amperometric microbiosensor that uses an immobilized biological interface to measure the concentration of an analyte in a specimen. It consists of a casing that narrows to an aperture having a diameter at the tip no greater than 4 μm; enclosed within the casing a reference electrode and a working electrode both immersed in electrolyte; within the aperture, an inner polymer film, an immobilized biological interface layer, and an outer specimen-compatible, non-virulent polymer film. Another important feature of the present invention is that the microbiosensor can readily be encased in a durable protective sheath. The microbiosensor is especially useful in situ for specimens that cannot be mixed, such as in situ compounds in unmixed fluid, or semi-solid specimens. The microbiosensor provides 90% response time less than 5 seconds and typically about 1 second, less than 5% change in output current due to changes in the stirring rate, and the ability to measure in viscous, semi-solid or porous-solid specimens with a spatial resolution as small as 30 μm.

15 Claims, 20 Drawing Sheets

OTHER PUBLICATIONS

*Polyurethanes in Medicine,* M.d. Lelah, Ph.D. et al., Chapter 5, pp. 57 & 205 no month or year available.

*Preparation of Porous Polyurethane Particles and Their Use in Enzyme Immobilization,* Biotechnol. Prog., X. Wang et al., 1993, 9, no month available 661–665.

*An Oxygen, Microsensor With A Guard Cathode,* Limnol. Oceanogr., 34(2), 1989, 474–478 no month available.

*Amperometric Processes With Glucose Oxidase Embedded In The Electrode,* Bioelectrochemistry and BHioenergetics, 28 (1992) 387–400, A Section of J. Electroanal. Chem. & Const. vol. 343 (1992) no month available.

*Microbial Sensors for Determination of Aromatics and their Chloroderivatives, Part II: Determination of Chlorinated Phenols* . . . , Appl. Microbiol Biotechnol (1993) 38:556–559 no month available.

*Immobilised Cells and Enzymes, A Practical Approach,* IRL Press 1985, ed. J. Woodward, pp. 41–42 no month available.

*Analytical Chemistry,* Alvarez–Icaza M., Bilitewski U. (1993) 65(11): 525 A no month available.

*Instrumentation and Sensors for the Food Industry,* Chapter 17, Ed. Erika Kress-Rogers, 1993, pp. 581–643 no month available.

*Virchows Archiv Abteilung B. (German) Cell Pathology,* Duncan, C.J. (1989) 56(4): 271 no month available.

*Fundamentals and Applied toxicology,* Durand–Cavagna et al. (1989) 13(3): 500 no month available.

*Applied and Environmental Microbiology,* in press, Emerson, D. and Revsbech, N.P. (1994) no month available.

*Applied and Environmental Microbiology,* Emerson, D., and Worden, M. and Breznak J.A. (1994), p. 1269 no month available.

*Journal of the American Diet Association,* Gropper S.S. et al. 93: 328 no month or year available.

*Analytical Chemistry,* Kim, Y.T., Scarnulis, D.M. and Ewing, A.G., (1986) 58: 1782–1786 no month available.

*Biosensors & Bioelectronics,* Karube I. et al. (1993) 8(3–4): 219 no month available.

*Biosensors,* Karube I. and Suzuki M., Oxford University press, New York, p. 155 no month or year available.

*IEEE Engineering In Medicine and Biology,* Karube I. and Nakanishi K. (1994) Jun./Jul. p. 364.

*Trends in Modern Meat Technology 2,* Proceedings of the International symposium, Den Dolder, Netherlands, 23–25 Nov. 1987, E. Kress–Rogers.

*Biophysical Journal,* Lai C.S. et al. (1987) 52(4): 625 no month available.

*Chemico–Biological Interactions,* Larsson R. et al. (1986), no month available 60(3): 317.

*Analytical Proceedings,* Biosensors of the Food Industry, May 1986, E. Kress–Rogers, E.J. D'Costa, vol. 23, pp. 149–151.

*Biosensors & Bioelectronics,* Luong et al. (1991), 6: 547 no month available.

*Diet and Carcinogenesis, Food Safety Assessment, ACS Symposium Series* Chapter 27 no month or year available.

*American Revue of Respiration Diseases,* Milton et al. (1990) 142(1): 84 no month available.

*Biochemical Pharmacology,* Nakagawa Y. and Moldeus P. (1992) 44(6): 1059 no month available.

*Archives of Toxicology (Berlin),* Neun D.J. et al. (1992) 66(1): 11 no month available.

*Protein Immobilization, Fundamentals and Applications,* Marcel Dekker, Inc., 1991, ed. R.F. Taylor, p. 40 no month available.

*ACS National Meeting,* Chicago, Aug. 1995, Peteu S.F., Worden R.M., Emerson D. (1955)—Presentation invited and abstract submitted.

*Analytical Chemistry,* Kim, Y.T., Scarnulis, D.M. and Ewing, A.G., (1986) 58: 1782–1786 no month available.

*Limnology and Oceanography,* Revsbech N.P. (1989) 34: 474 no month available.

*Applied Microbiology and Biotechnology,* Scheller F. (1993), no month available 38: 556.

*Biotechnology and Applied Biochemistry,* Simmons, D.M., Kearney J.N., (1993), 17(1): 23 no month available.

*Analytical Chemistry,* T. Abe, Y.Y. Lau and A.G. Ewing (1992) 64: 2160–2163 no month available.

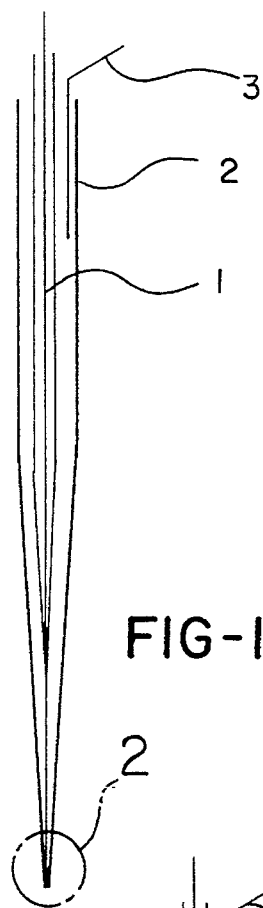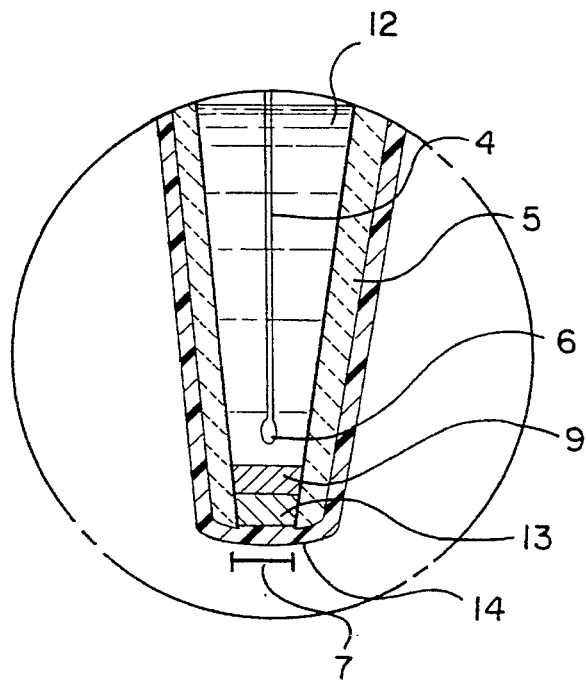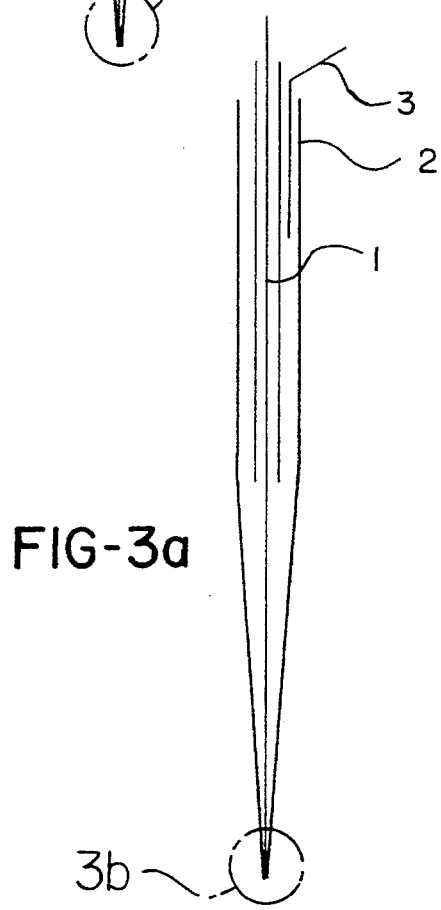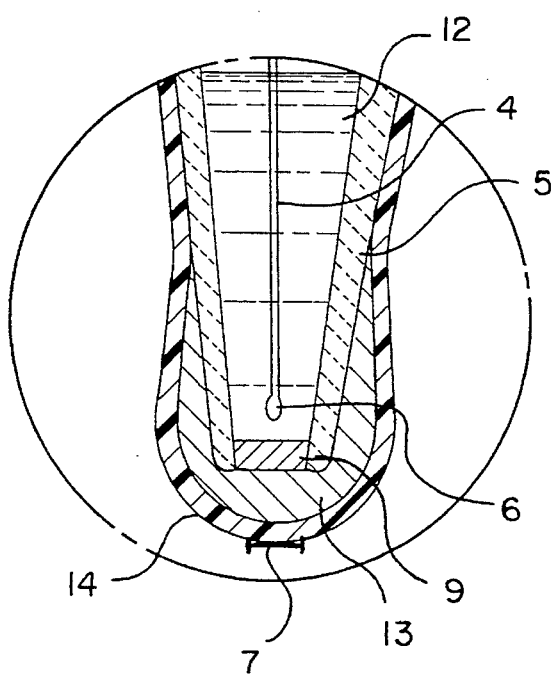

MICROBIOSENSOR USED IN-SITU

TECHNICAL FIELD

The invention relates to needle-type, amperometric, internal referenced biosensors with an ultra-small tip, sensors that use immobilized microorganisms to measure in situ the concentration of an analyte in a fluid, viscous or soft solid specimen.

BACKGROUND OF THE INVENTION

The biosensor literature consists of numerous publications (patents, articles, and books) per year. A short description of the mode of operation of biosensors is given below. Then, several publications relevant to this patent are described, along with a comparison of their features to those of the present invention.

Biosensors consist of a biological interface (e.g., an enzyme or cell layer) coupled to a transducer (e.g., an oxygen electrode). The biological element gives selectivity and specificity for detecting specific analyte molecules. The interaction of the biological element with the analyte is measured by the physical transducer. In the case of electrochemical biosensors, the transducer is typically an electrode.

Electrochemical biosensors often have a membrane separating the electrode from the surrounding liquid. The relative rates of analyte transport to the electrode and electron transfer at the electrode affect the performance properties of the biosensor. The overall transport resistance is the sum of the resistances in the membrane and the stagnant liquid film adjacent to the membrane. If the liquid-film resistance is significant, the probe's response is dependent on the local liquid velocity, which is typically controlled by the rate at which the specimen is stirred. To prevent stirring dependency, the resistance of the membrane can be increased. However, this approach leads to slow probe response times. Thus, there is typically a tradeoff between the speed of the probe's response and the rate at which the liquid sample is stirred. For specimens that cannot be stirred (e.g., in situ measurements within highly viscous or semi-solid samples), conventional biosensors give slow or inaccurate readings.

Due to their extremely small size and rapid electron transfer, microbiosensors can provide both rapid response characteristics and independence of stirring rate. Thus, they are especially well-suited for applications that require rapid, repetitive measurements, especially where stirring may not be possible. Their extremely small tip size also allows accurate measurements within small specimens, measurements of concentration gradients with high resolution, and measurements inside of samples with minimal surface disturbance. Several ideal application areas are listed below:

Monitoring food quality and safety, such as the degree of freshness and the concentration of toxicants.

Measuring gradients within biofilms, and other small-scale ecosystems.

Monitoring the activity of single cells, such as neurotransmission events.

An electrochemical biosensor is developed in the world patent application WO/PCT 92/04438 by Eisenhardt and Christiensen from Radiometer A/S, Copenhagen, Denmark (1992). It consists of a working electrode and a reference electrode. The base part contains a working electrode in the form of platinum wire that has 250 µm diameter. The laminated outer membrane consists of a 15 µm thick protective layer. This microsensor is several centimeters in diameter and is similar in many aspects to the type E909, sold by Radiometer. Its main drawbacks, if compared with the present invention disclosure, are slower response times, sensitivity to stirring, and its use limited to liquid samples drawn from the process.

The antibody-antigen biosensor for determining lactate dehydrogenase-5 was devised by Risphon et al. (1993, U.S. Pat. No. 5,147,781). Antibodies were bound directly to an electrically conductive electrode. However, these antibodies are difficult and time consuming to prepare and their extremely high affinity makes the dissociation kinetics slow, which makes the sensor response slow.

A single-chip, planar shape receptor-based biosensor is described (1993) by Taylor et al., Arthur D. Little Inc., Cambridge, Mass., in U.S. Pat. No. 5,192,507. In particular, acetylcholine receptor and opiate receptor have been immobilized in a polymeric film made with bovine serum albumin, gelatin and glutaraldehyde. An in situ repetitive use has not been considered for these microelectronic biosensors. Another disadvantage of this type of biosensor is that an adequate method for fixation and sealing of the diffusion-limiting membrane around the electrode perimeter has not been developed (Alvarez-Icaza and Bilitewski, 1993). Moreover, this probe uses glutaraldehyde, which is known to be cytotoxic (Simmons and Kearney, 1993) and therefore unsafe for some biosensor applications.

"Ultrasmall" glucose sensors have been constructed for voltammetry and amperometry (Abe, Lau and Ewing, 1992; Kim, Scarnulis and Ewing, 1986) by using platinum deposited carbon ring microelectrodes with glucose oxidase. The 2–10 µm sensing tip allowed average response times of 0.8 seconds. The detection limit is reported as 50µM, and the linear range is up to 5 mM. Nevertheless, the amperometric measurements are carried out in a two-electrode mode, which is difficult to perform in situ. Another drawback is that the sensor produces a noisy signal, so that a copper mesh Faraday cage is required as an electromagnetic shield. Moreover, this microsensor design includes a mercury film, which is toxic. Other problems are the electrode fouling and the short stability span, of only "a few hours". The microbiosensor of this invention has proved a lower and better detection limit of less than 10µM and good stability after multiple tests over a period of time, e.g., 6 consecutive months. The present application has low electrical noise. Both the reference and the working electrodes are situated inside the sensor case, behind an electrically insulating silicone film, and bathed in an electrolyte solution such as 1M KCl. The electrolyte also serves as an electrical shielding from the cathode. The signal from the microelectrode is therefore expected to have an extremely low noise and to be very stable, with a current drift less than 2% per day.

Other miniature enzymatic biosensors are made using carbon fibers, e.g. U.S. Pat. No. 5,186,808, by Yamaguchi and co-workers (1993) from Terumo K.K. Company, Tokyo, Japan. This particular graphite electrode has an electrical conductive substrate with a sectional area of less than $10^{-5}$ cm$^2$, which means the electrode hole diameter is about 35.7 µm. The major drawback of this patent is that the enzyme sensor is used in a three electrode cell. The use of three electrodes, some of which may not have microscopic tip dimensions, would make in situ measurements difficult or even impossible. By contrast, the present microbiosensor has all electrodes built in one case. In addition to greater convenience, this integration also results in reduced electrical noise levels. Also, the sensitivity reported by Yamaguchi et al. for glucose is low, 1 mM, when compared with the present microbiosensor.

Other sensors based on carbon fibers (Karube et al., 1993) or of solid-state type (Kawaguri et al., Matsushita Co., Japan, U.S. Pat. No. 5,171,689) report the use of 1, 4-benzoquinone or ferricyanide as electron mediators/oxidizing agents. Unfortunately, both 1, 4-benzoquinone and ferricyanide may be toxic. Benzoquinone toxicity has been proven, including for short term bacterial bioassays (Trevors and Basaraba, 1980), isolated rat hepatocytes (Nakagawa and Moldeus, 1992) or mice bone marrow cells (Neun et al., 1992; Larsson et al, 1986). Ferricyanide was shown to have an embryotoxic action (Besedina and Grin, 1987), is relatively toxic to mammalian cells (Lai et al, 1987) and may cause structural damage on the skeletal muscle (Duncan, 1989). These two toxic mediators could potentially leach into the sample.

An optical biosensor is reported (1992) by Morris and colleagues from Baxter Diagnostics Inc., Illinois, in the world patent application WO92/12413, to detect microorganisms in a blood culture bottle. This application, and many other biosensors using a fiber optic transducer, have the disadvantages of being subject to interference from ambient light (Luong et al., 1991), usually requiring high energy sources and often suffering from a narrow concentration range.

Microbial biosensors (e.g. Scheller, 1993; Lee et al., 1992; Karube and Suzuki, 1990) are yet another method, which incorporate a microorganism as sensing element and can measure the respiration activity (detected by an oxygen sensor) or electroactive metabolites, such as $H_2$, $CO_2$, $NH_3$ and organic acids, secreted by the microorganisms. Although these sensors may exhibit a long shelf life and are more pH and temperature tolerant if compared to the enzyme probes, these microbial sensors have a longer response time, need more time to return to the base line and additional care must be taken to ensure selectivity (Karube and Nakanishi, 1994).

It is an object of the present invention to describe a microbiosensor having a needle-type, e.g., cylindro-conical configuration with a sensing tip aperture not greater than 25 (preferably 4) micrometers ($\mu m$) and having the ability to be compatible with the specimen or host such that the outer protecting membrane that is utilized is non-virulent thereto.

Also of interest are the following U.S. Patents:

U.S. Pat. No. 4,680,268 describes an implantable biosensor and a method for sensing products. A closed chamber for containing oxygen to supply oxygen through a membrane for the enzymatic reaction is described. However, the sensor does not appear to be of the micro-type. The precise geometry and functional characteristics (e.g. life span, range and detection limit) are not specified.

U.S. Pat. No. 4,871,440 describes a biosensor which has a foundation electrode comprising of a working electrode, a reference electrode and a counter electrode arranged on a planar surface.

U.S. Pat. No. 5,120,420 describes a planar type biosensor where a biological sample solution is brought into contact with the inlet 10 of the biosensor while the air within the space 8 is rapidly discharged through the outlet 11.

U.S. Pat. No. 5,177,012 describes a biosensor containing immobilized *Zymomonas mobilis* cells for measuring glucose, fructose and sucrose.

U.S. Pat. No. 5,185,256 pertains to a biosensor where the electrode system is formed mainly of carbon and is integrally combined with a perforated body so that washing the electrode system is unnecessary. The planar electrode system is formed on a substrate and is primarily made of carbon in a perforated body having an enzyme and electron acceptor.

U.S. Pat. No. 5,223,124 is a monolayer needle electrode having a core platinum anode (2) situated inside a stainless steel reference cathode (4). The stainless steel tube has an outer diameter of 0.46 mm. The enzyme is immobilized onto angular surface A. The immobilization of a polypeptide such as an enzyme was performed by blending the enzyme in a polymeric matrix such as an aqueous polyurethane dispersion which is applied to the angular member A. The detection limit for glucose appears to be 2.4 mM. The biosensor is usable 5–24 hours.

U.S. Pat. No. 5,286,364 described an electrode for a biosensor, wherein the analyte sensing agent is an enzyme which is embedded in a polymer but with a number of its analyze recognition sites unblocked. FIG. 15 is a graph of the glucose concentration v. steady state current. The working electrode of the biosensor is used in a flow cell injection system, of the three-electrode type. The microbiosensor features a detection limit of approximately 50$\mu M$ with a response time of 1–2 minutes.

U.S. Pat. No. 5,288,636 describes a probe for glucose using a redox mediator of ferricyanide.

Other patents of interest are: U.S. Pat. Nos. 5,288,613; 5,356,786; 5,225,064; and 5,334,296.

In summary, the biosensor systems described previously are subject to one or more of the following drawbacks relative to the present invention: slower response times, stirring dependency, necessity of diluting the sample before measurement, narrower concentration range, use of potentially toxic electron mediators, high levels of electrical noise, and poor long-term stability.

SUMMARY OF THE INVENTION

The present invention is a novel, ultra-small tip, needle-type and internal referenced, amperometric microbiosensor that uses an immobilized biological interface, e.g., a microorganism, to measure the concentration of an analyte in a specimen. The microbiosensor is especially useful for specimens that cannot be mixed, such as in-situ compounds in unmixed fluid, or semi-solid specimens. It consists of a casing that narrows to a tip having a diameter no greater than 40$\mu M$; within the tip is an aperture no greater than 10, preferably 4$\mu M$, that contains a semi-permeable membrane. Enclosed within the casing is a reference electrode and a working electrode both immersed in electrolyte; an immobilized biological interface layer into the aperture or onto the tip, and an outer specimen-compatible, non-virulent polymer film. The inner film prevents co-mingling of the electrolyte solution and specimen compounds. The immobilized enzymes or cells act as a selective, biological interface between the analyte and the working electrode. The outer polymer film protects the biological interface and excludes compounds that may interfere with the probe's performance.

Described is cylindro-conical type microbiosensor for testing a specimen comprising, a casing having a tip no greater than 12 micrometers;

enclosed within the casing an anode, a cathode and an electrolyte disposed there between; and juxtaposed to the aperture of the casing, an immobilized biological interface capable of measuring an analyte in the specimen.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a schematic diagram of the microelectrode of the present invention;

FIG. 2 is a exploded view of a portion of FIG. 1 wherein the circle shows the microelectrode of the present invention;

FIG. 3a is a schematic diagram of the microelectrode of the present invention;

FIG. 3b is an exploded view of a portion of FIG. 3a showing an alternative embodiment where the biological interface is shaped onto the tip.

DETAILED DESCRIPTION OF THE INVENTION

Figure 4:
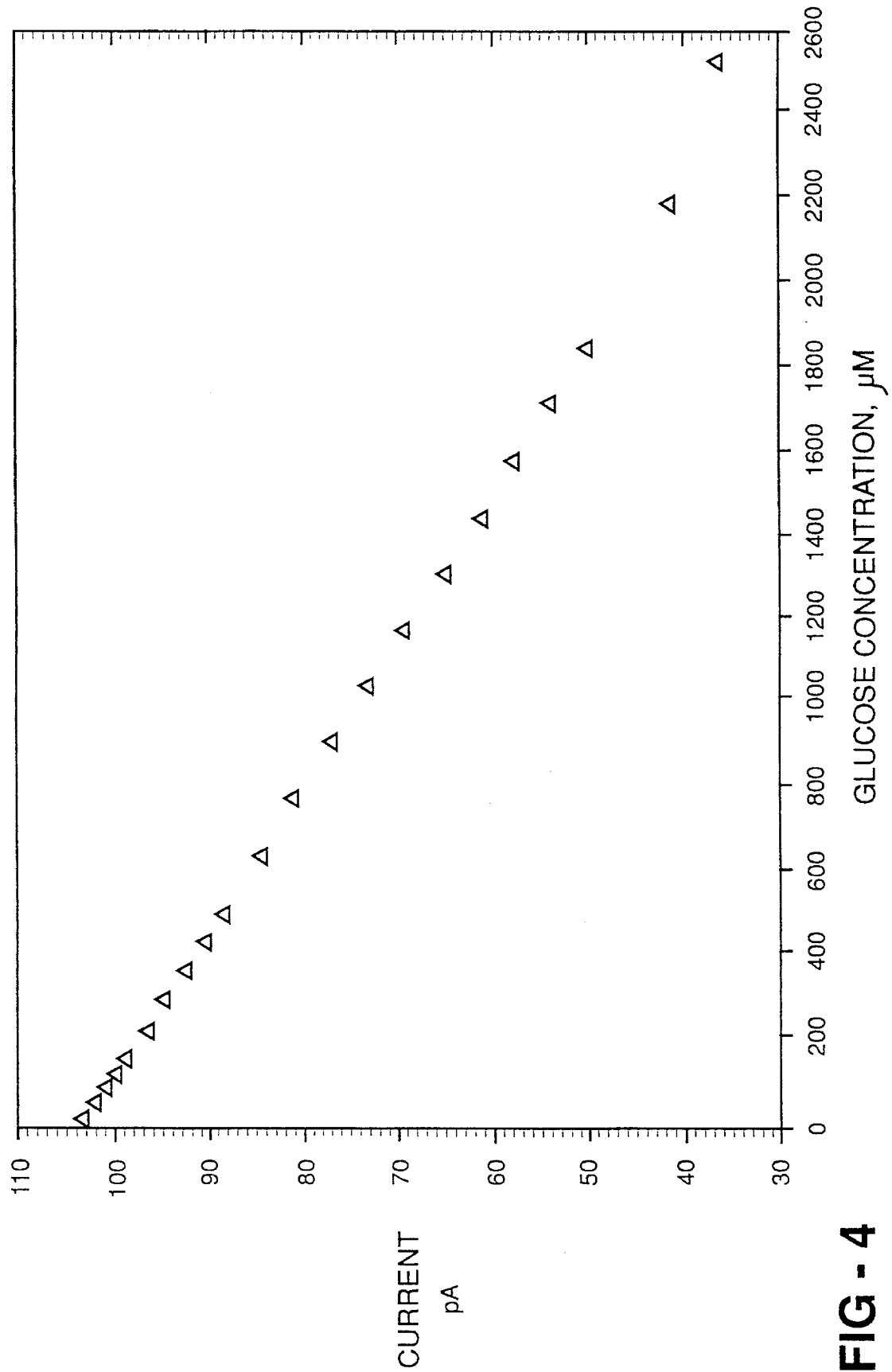
FIG. 4 is a chart plotting current versus glucose concentration utilizing the microbiosensor of the present invention.

The present invention is concerned with a microbiosensor. It can be prepared as follows:

The amperometric oxygen microelectrode (FIG. 1) consists of a cathode 1, a case 2, and an anode 3. The cathode is made from 0.3 mm diameter platinum wire 4 that is electrochemically etched in a saturated cyanide solution to a very fine tip of 1–5 μm. The wire is inserted into a tapered green-glass tube 5. The untapered end of the tube is then fused in a propane flame to a soda-lime-glass tube that forms a shaft. An electric microforge is used to fuse 1.5 to 2 cm of the tapered green glass to the wire. The glass at the tip of the wire is gently heated, causing it to retract and expose about 10 μm of the wire at the tip, which is then electroplated with gold 6, using an optical microscope and a micromanipulator. One of the oculars has incorporated a micrometer reticle calibrated for micrometers, so that the whole micro-manufacturing and micro-assembling process can be performed with an adequate precision and reproducibility.

The case, which ultimately contains the cathode, is made from a soda-lime-glass Pasteur pipette that is pulled in a propane flame to give a fine, tapered capillary 2 to 10 μm in diameter. The capillary is broken using a tweezer, leveled and heated under the microscope to constrict the tip aperture 7 to about 1–2 μm. The tip is then dipped into silicone, under microscope using the micromanipulator, giving a 5–10 μm thick silicone membrane 9. After the silicone has cured, the cathode is inserted into the case until the cathode tip comes within about 10 μm of the silicone membrane and the shaft is then partially glued to the case with a droplet of epoxy resin adhesive.

The anode is made out an Ag/AgCl wire, with a diameter of 0.25 mm. The microelectrode is completed by adding electrolyte 12 1M KCl and the anode into the case and sealing all openings with adhesive.

The calibration consists in applying a polarization voltage of −750 mV at the working electrode (the cathode) with respect to the reference electrode (the anode). Then, by immersing the microprobe into a phosphate buffer (pH 7.5) and bubbling nitrogen or oxygen/air through this liquid, the zero and 100% values of the sensor can be established from the picoammeter readings.

To add the biological interface (FIGS. 2 and 3), the microelectrode is tipped with a porous layer or film of immobilized biocatalyst, e.g. an oxidase enzyme, commercially available for a variety of substrates. The glucose microbiosensor, for example, essentially consists of an amperometric oxygen microelectrode tipped with immobilized glucose oxidase (GOx) that catalyzes the reaction:

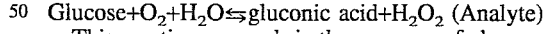

Glucose+$O_2$+$H_2O$⇌gluconic acid+$H_2O_2$ (Analyte)

This reaction proceeds in the presence of glucose, and the resulting consumption of oxygen causes a decrease in the probe's current. If the glucose concentration is rate-limiting, the electrode's response decreases monotonically with increasing glucose concentration. Thus, the GOx microsensor may be calibrated and then used as a glucose sensor.

The biological interface therefore aids in measurement of the analyte by its catalytic action. The variation in current is dependent on the analyte concentration within the specimen.

The biological component may be immobilized onto the electrode tip in at least two alternative ways.

The first is to force both the silicone 9 and biological interface 13 (immobilized in a polyacrylamide solution) into the tip of the case (FIG. 2). The second way is to simply apply an ultra-small droplet of the polyacrylamide-biocatalyst mixture onto the tip (FIG. 3). The gel is then allowed to cure to 6–10 hours at room temperature. To date, the second method has been easier to do, but the former method allows better control of the ultimate tip diameter and protects the enzyme layer within the glass tip.

Several initiator systems for acrylamide polymerization procedures and physical entrapment of the biological interface were initially tried: (ammonium persulphate+heat), (riboflavin+visible light) and [ammonium persulphate+tetraethylmethylenediamine (TEMED)]. The most successful appears to be the last method.

Two types of membrane films were tried as protective outer layer 14, applied over the polyacrylamide biological interface gel: cellulose acetate and polyurethane. Both materials are generally accepted as safe and non-toxic in contact with living specimens. Some problems with cellulose toxicity have been suggested: corneal toxicity in rabbits (Durand-Cavagna et al., 1989) or intratracheal in hamsters (Milton et al., 1990). Extensive studies showed no toxic effects of polyurethane, and it gives high flexibility, toughness, excellent dimensional and hydrolytic stability (Planck et al., 1987). The polyurethane makes a more stable protective membrane than cellulose acetate.

The polyurethane solution is prepared by making a mixture of 98% tetrahydrofuran and 2% N,N-dimethylacetamide and dissolving polyurethane in it to a final concentration of 5% (w/v). The sensor tip is dipped into this solution a couple of times, and then the solvent is allowed to evaporate at a room temperature for 5–8 hours.

It is to be appreciated that the microbiosensor of the present invention has primary applicability in a number of food related processes. Accordingly, therefore, the components that come in contact with the food such as the outer polymer membrane and the needle should be compatible with the specimen being tested. The utilization of the terminology "non-virulent" means that it should not be toxic or poisonous to the specimen being tested. In other words, the micro biosensor would be stable in the environment of the specimen for the period of time that the testing occurs.

The sensor of the present invention can be used to detect a number of analytes using a variety of biological interfaces, e.g., enzymes, particularly directed towards the desired substrate. In other words, the biological interface, e.g., enzyme that would be immobilized would vary depending upon the material to be detected. In general, the sensor is preferably an oxygen sensor although other sensors are applicable depending upon the enzyme to be utilized. The materials that can be tested include sugars such as fructose, sucrose, lactose, galactose and other analytes such as hydrogen peroxide and choline. In general any substance that would be present in a fluid, viscous or semi-solid specimen may be detected utilizing the technique of the present invention. Examples or specimens may be biological fluids, food samples, biofilms, single cells, and the like.

The microbiosensors of the present invention offer several advantages over other biosensors, including (i) stirring insensitivity; (ii) the ability to non-destructively measure analyte concentrations in situ within unmixed liquid, viscous, and semi-solid specimens having a volume as small as a few microliters; (iii) response time of a few seconds (iv) high sensitivity; low levels of background electrical noise; (v) repetitive use for extended time; (vi) may be encased within protective sheaths for durable use in field or industrial settings; (vii) potential for low cost per measurement.

Having described the invention in general listed below are preferred embodiments wherein all percentages are percent by weight, and all temperatures are degrees centigrade unless otherwise indicated.

EXAMPLE 1—Calibration of the Microbiosensor

A typical calibration curve for the glucose microbiosensor is shown in FIG. 4. The characteristics of other enzyme amperometric enzyme microbiosensors are reported later on, for detecting lactose (FIG. 8), galactose (FIG. 7), choline (FIG. 9) and hydrogen peroxide (FIG. 10).

Glucose depletion at the surface of the meat is caused by the activity of the microbial flora. Once glucose is depleted, amino acids are broken down, with the production of toxic amides (Kress-Rogers et al., 1992); therefore glucose can be used as a freshness indicator.

The Glucose oxidase EC 1.1.3.4., from *Aspergillus niger*, grade VII-S, with the activity off 10,000–20,000 units/mg solid is purchased from Sigma Chemical Co., St. Louis, Mo. The enzymes used, including the β-galactosidase EC 3.2.1.23, from *Escherichia coli* grade VI with 320 units/mg solid, the Galactose oxidase EC 1.1.3.9. from *Dactylium dendroides*, and the catalase EC 1.11.1.6 from bovine liver 41,000 units/mg protein, are from Sigma Chemical. The Choline oxidase EC 1.1.3.17. from *Alcaligenes* species with 13–16 units/mg solid is from ICN Biomedicals, Aurora, Ohio.

The green glass (Schott 8533) and soda lime glass (Schott 8414) are from Schott Glasswerke, Mainz, Germany. The bicomponent resin hardener adhesive gel is made by Devcon Corp., Wood Dale, Ill., and the silicone gel used to make the microprobe membrane is SYLGARD 527, from Dow Corning, Midland, Mich.

The optical microscope is Olympus CH-2, Japan; the microforge is built by Michigan State University, Microelectrode Laboratory and the calibration chambers were from Koh Development, Ann Arbor, Mich.

The microprobes' signals are measured by a picoammeter made by Diamond General, Ann Arbor, Mich. and recorded by the dual flat bed recorder BD211, Kipp & Zonen, Delft, Netherlands.

The oxygen microprobes are built generally using the method from Aarhus Universitet, Denmark (Revsbech, 1989).

Performance data for the glucose microbiosensors (FIG. 4–6) show detection limits of 1–10μM, response times of 0.5–1.5 sec., linear ranges of 0–10 mM and sensitivities of 10–100 pA/mM.

EXAMPLE 2—Selectivity of the Microbiosensor

Figure 5:
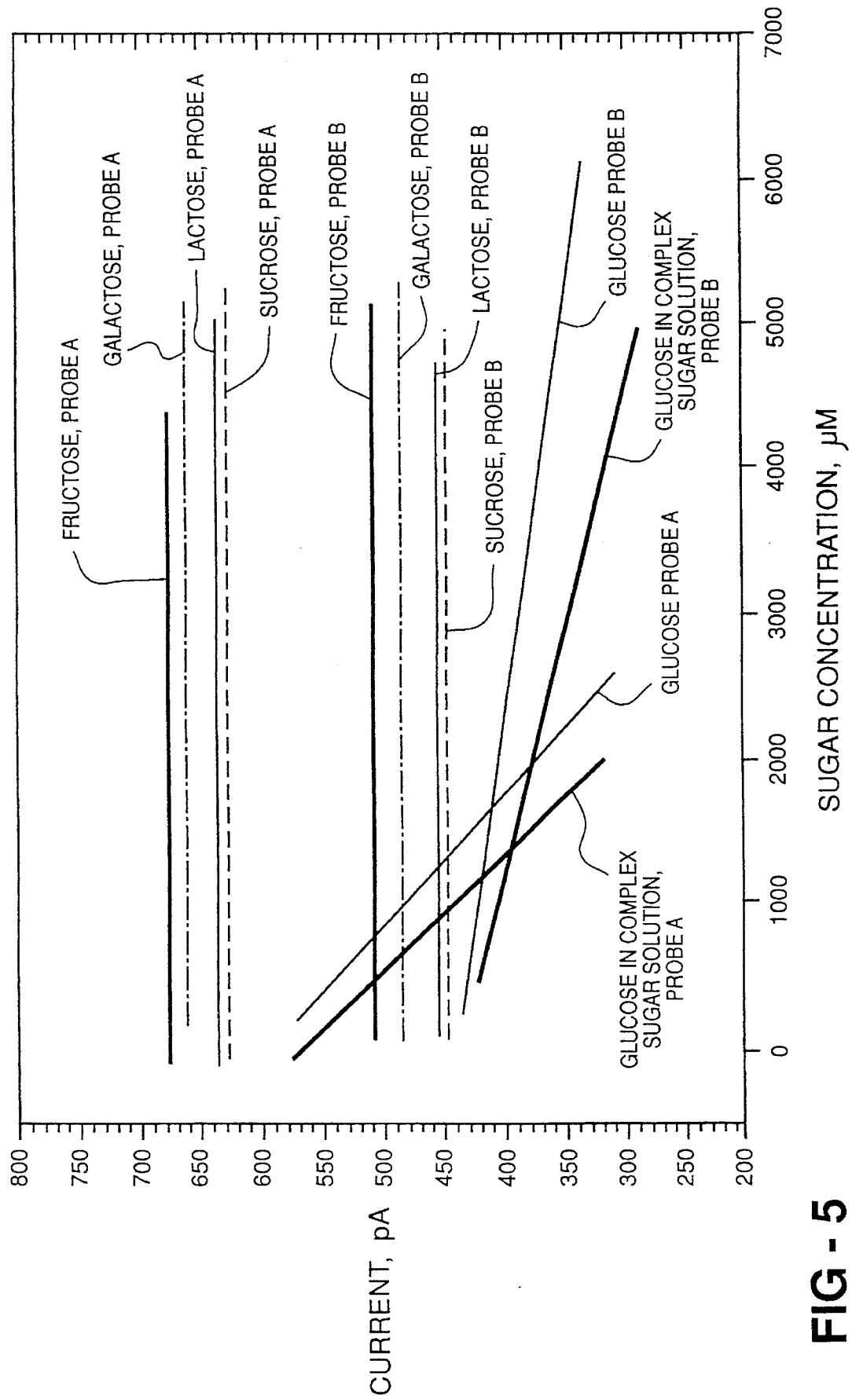
FIG. 5 shows the selectivity of measuring glucose in a sugar mixture for the microbiosensor of the present invention.

The glucose microbiosensors of the present invention show good selectivity which is demonstrated by very low, if any, responses to other sugars, like fructose and sucrose and the performance in a complex sugar solution containing 2% each of fructose, galactose, sucrose and lactose (FIG. 5).

These sensors have been operational after 50 tests during up to 6 consecutive months period of time.

EXAMPLE 3—Lactose Microbiosensor

Lactose intolerance in humans is based on an inherited deficiency in the activity of enzyme β-galactosidase in the intestine (Taylor et al., 1992).

Figure 8:
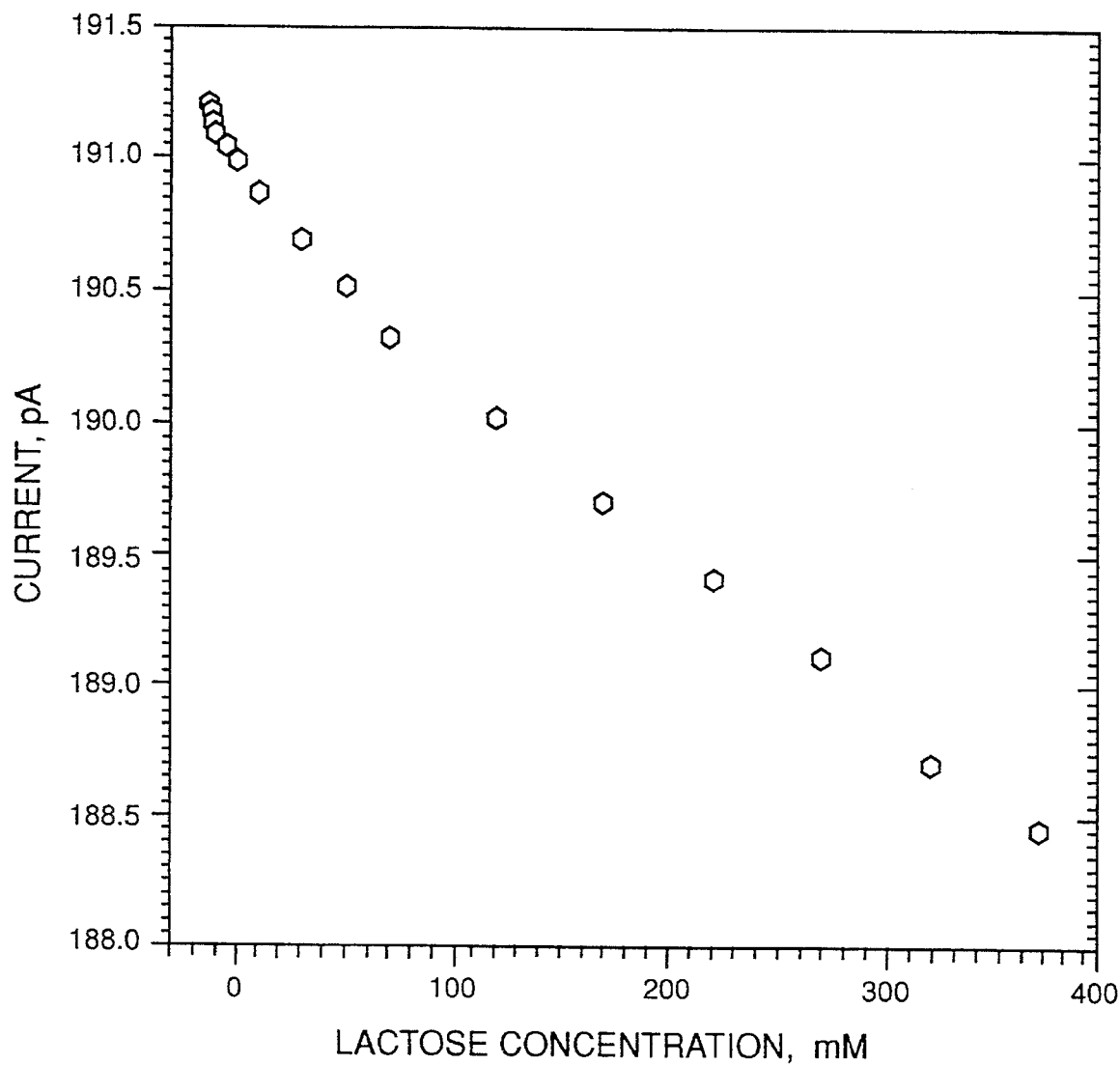
FIG. 8 is a calibration chart plotting current versus lactose concentration utilizing the micro biosensor of the present invention.

Prototype lactose microprobes have had detection limits close to 500μM and linear ranges of 0.5–400 mM (FIG. 8).

EXAMPLE 4—Galactose Microbiosensor

The need for suitable methods for early detection of galactosemia and galactose intolerance has prompted the need for galactose detection in blood (Taylor et al., 1992) or food (Gropper et al., 1993; O'Connor et al., 1992).

Figure 7:
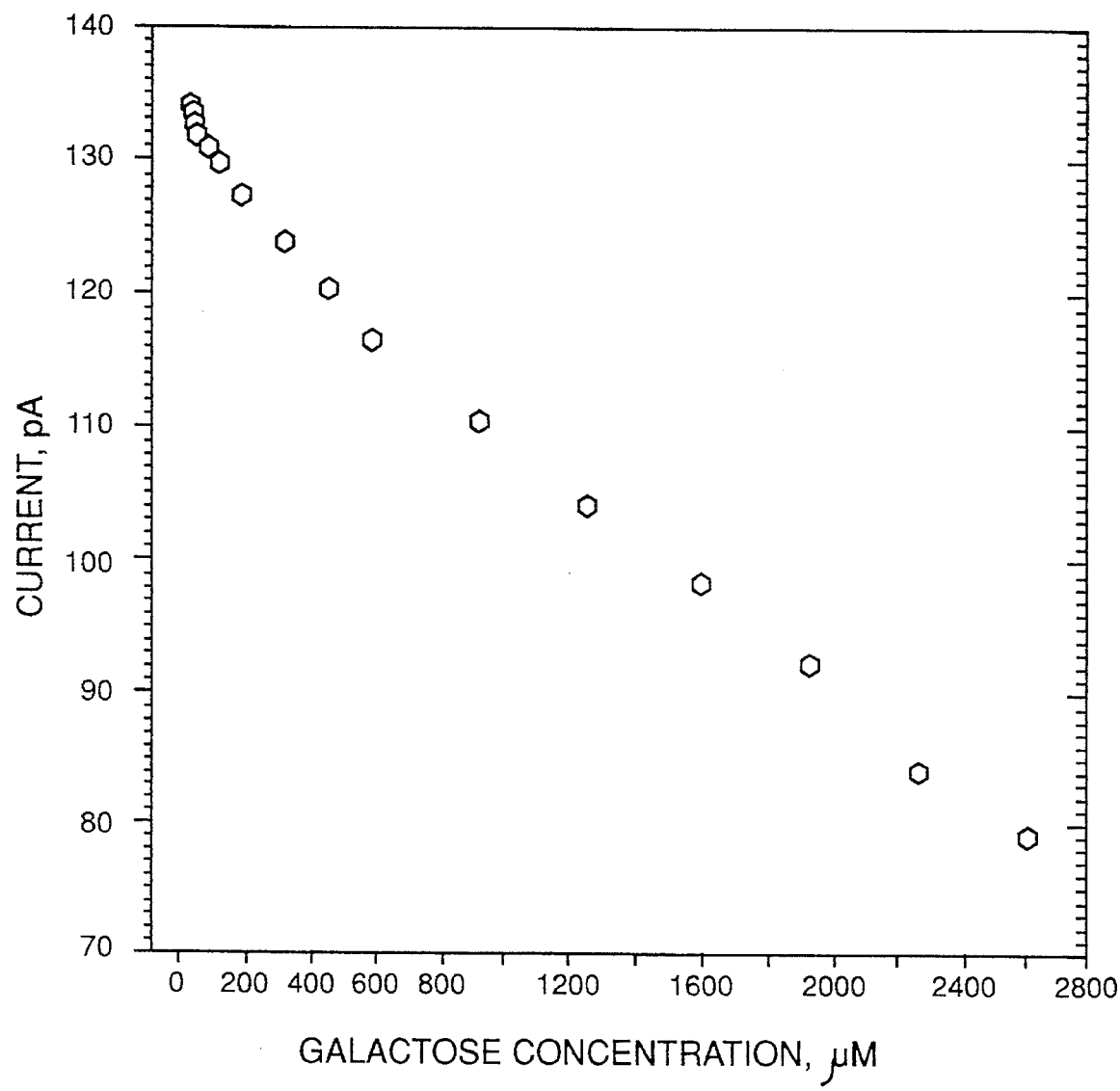
FIG. 7 is a calibration chart plotting current versus galactose concentration utilizing the micro biosensor of the present invention.

Prototype galactose microprobes have had detection limits of 1–10 µM and linear ranges of 0–7 mM (FIG. 7).

EXAMPLE 5—Choline Microbiosensor

Choline dietary deficiency produces pathologic lesions in organs, enhances the initiating potency of several carcinogens and may directly increase hepatic and other tumor formation (Milner, 1992; Hayatsu, 1991). Choline detection is also useful as a screening test for anticholinesterase activity, to evaluate the pollution caused by organo-phosphorus pesticides and other compounds with similar toxicological behavior. The use of insecticides by farmers (e.g., in Europe) is a serious problem for both the equilibrium of aquatic ecosystems and food contamination.

Figure 9:
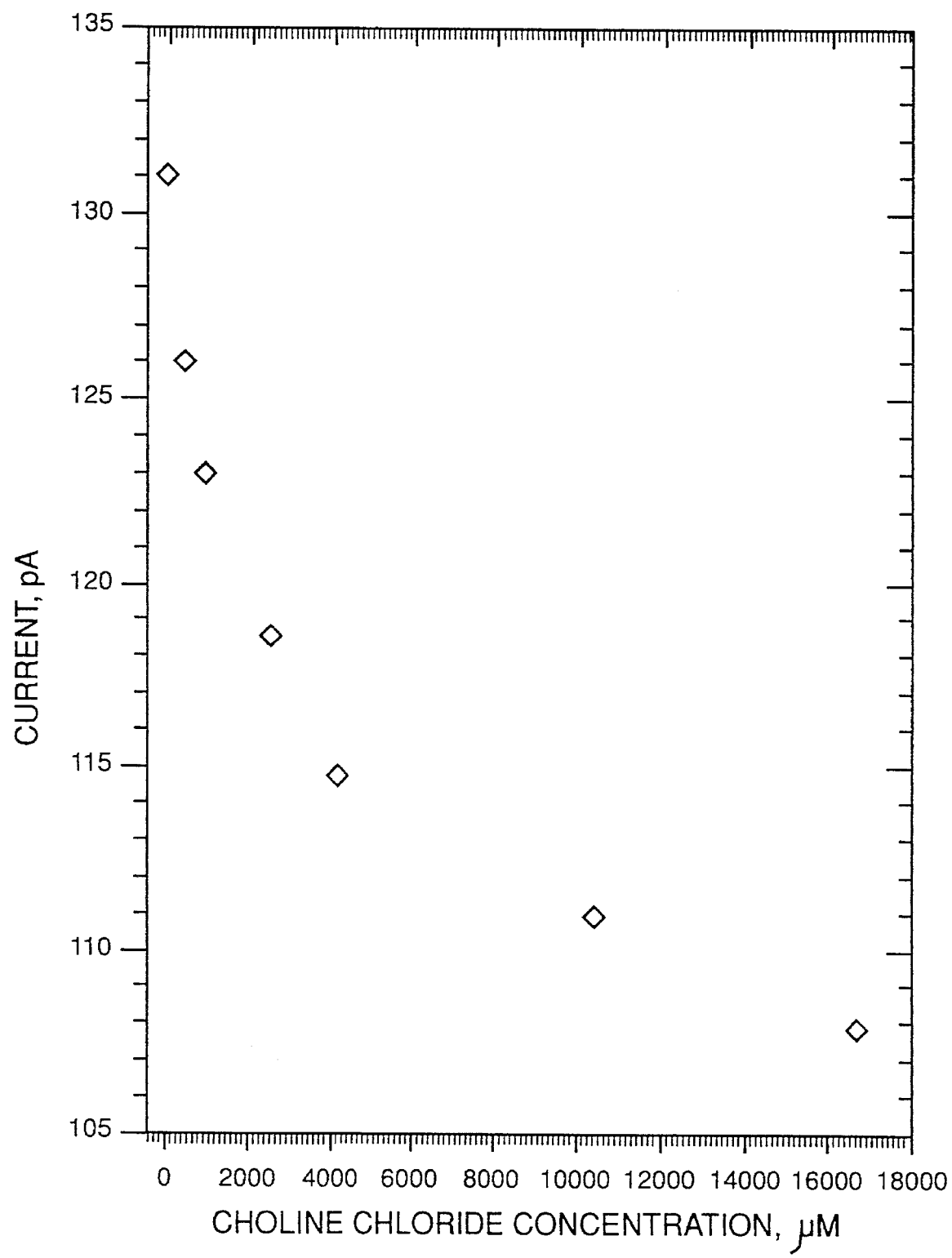
FIG. 9 is a calibration chart plotting current versus choline concentration of the microbiosensor of the present invention.
Figure 10:
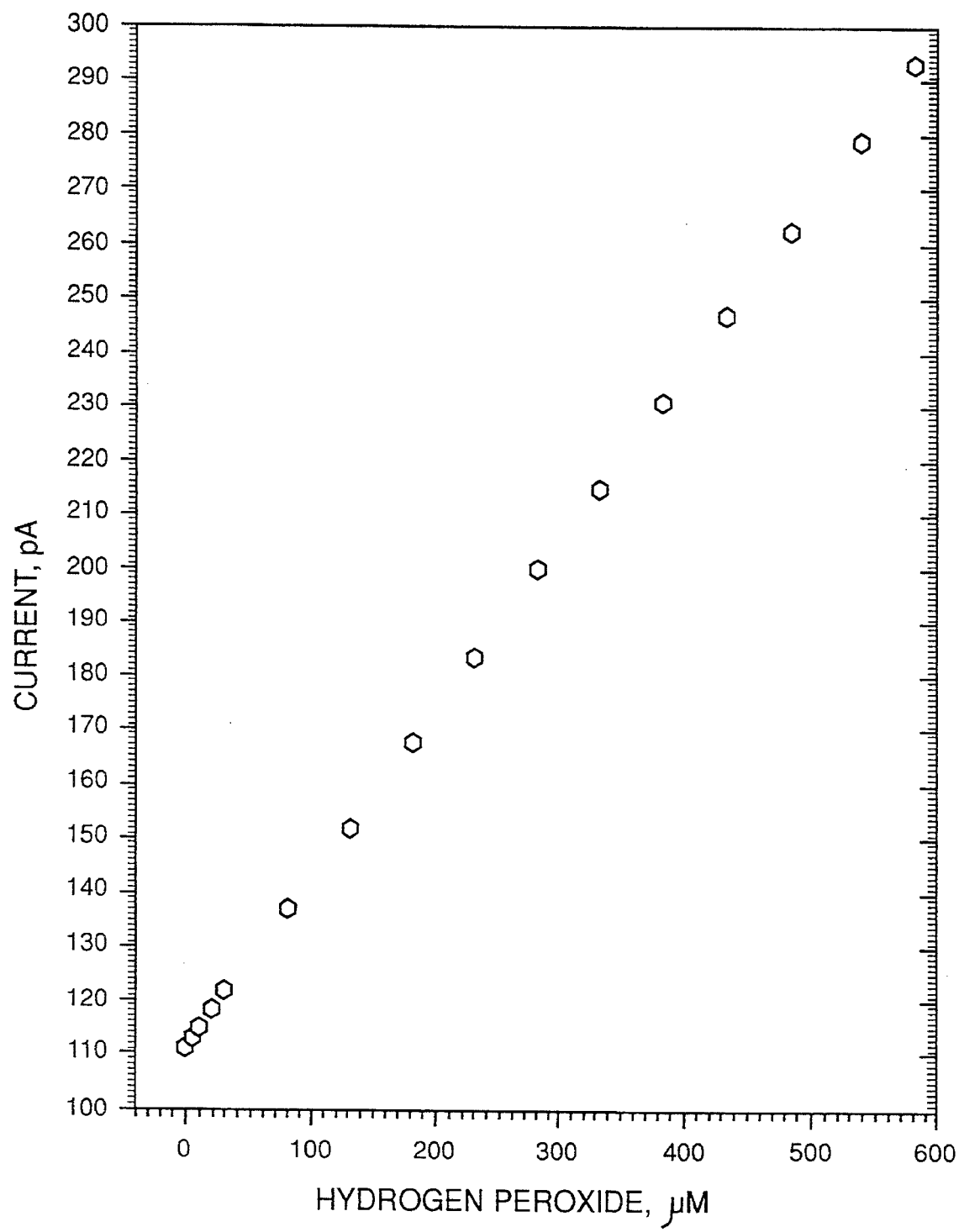
FIG. 10 shows a hydrogen peroxide calibration utilizing the microbiosensor of the present invention.

Prototype choline microbiosensors work with ranges of 0–10 mM and have had detection limits of 5–15 µM (FIG. 9).

EXAMPLE 6—Microbiosensor for Hydrogen Peroxide

Hydrogen peroxide ($H_2O_2$) is used in food industry as a bleaching and antimicrobial agent. Its toxicity, while difficult to detect with the standard tests, was proved by in vitro cytogenetic tests for several cell lines [Ishidate M., Jr., 1991]. It induced duodenal tumors in mice by administration of 0.4% in drinking water. For tea and coffee, hydrogen peroxide has been showed to play an essential role in mutagenicity, at levels of 100–200 µM [Aeschbacher, 1991].

The toxicity of $H_2O_2$ was investigated for human embryonic fibroblasts [Oya et al., 1992 and 1995] and also for DNA, enzymes and fatty acids [Proca et al., 1993]. Peroxide toxicity was determined by studies on guinea pigs, CHO cells, bovine tracheal myocites and rat cardiac myocites [Misawa and Arai, 1993; Abe et al., 1994; Cantoni et al., 1994]. It also has been frequently reported to induce or augment DNA damage [Luo et al., 1994; Martins and Meneghini, 1994] with implications for asbestos carcinogenesis [Mahmood et al., 1994]. The frequency of mutation of *Escherichia coli* genes increased by up to 30 fold, proportional with the $H_2O_2$ concentration [Akasaka and Yamamoto, 1994].

The hydrogen peroxide microbiosensor was built with an immobilized film of catalase. Detection limit was as low as a few µM, and the linear range extended from 0 to about 2.5 mM. A typical calibration curve for the $H_2O_2$ microbiosensor is shown in FIG. 10.

Figure 12:
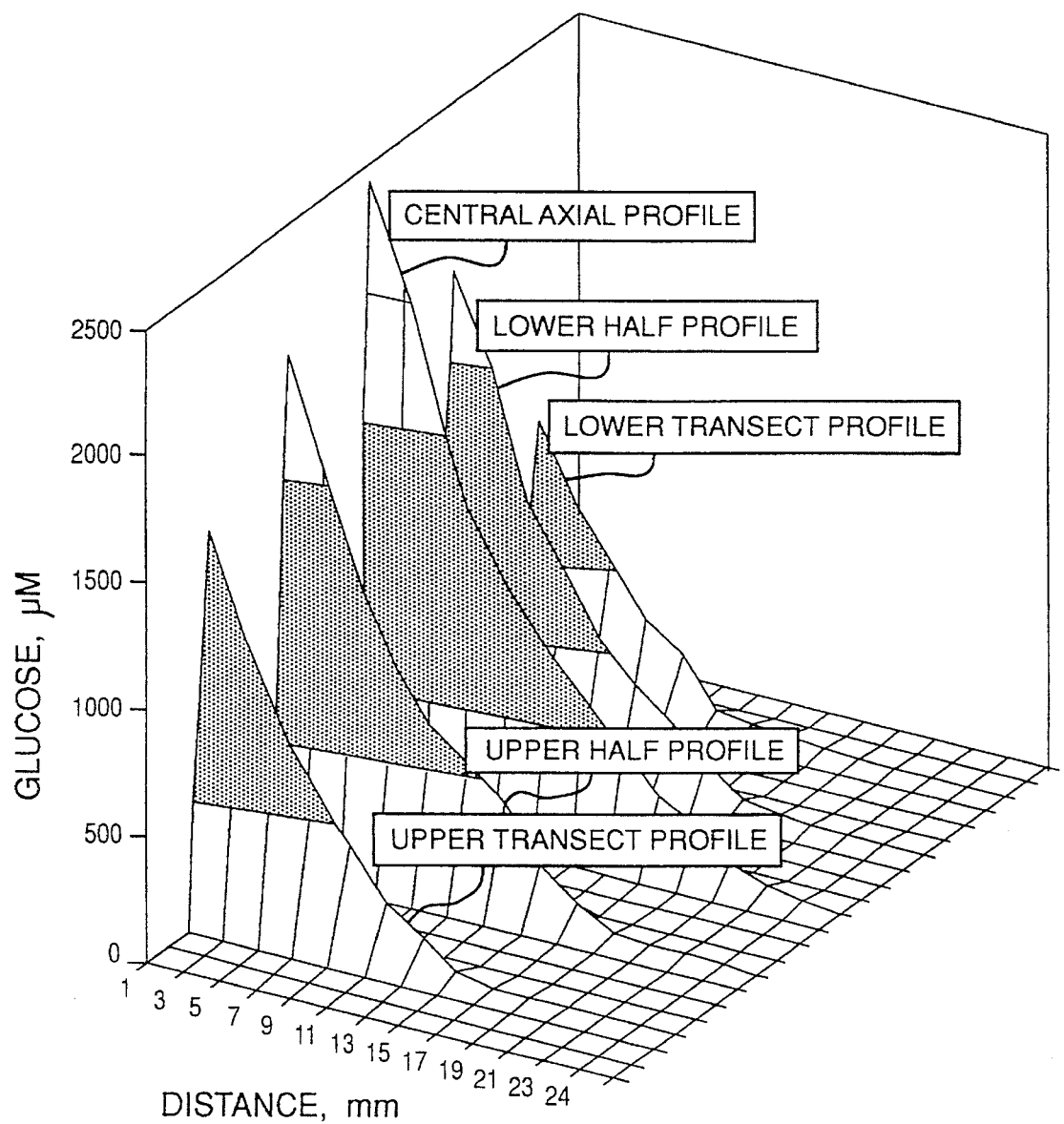
FIG. 12 shows glucose gradient profiles across the diffusion gradient chamber as measured with the microbiosensor of the present invention.
Figure 13:
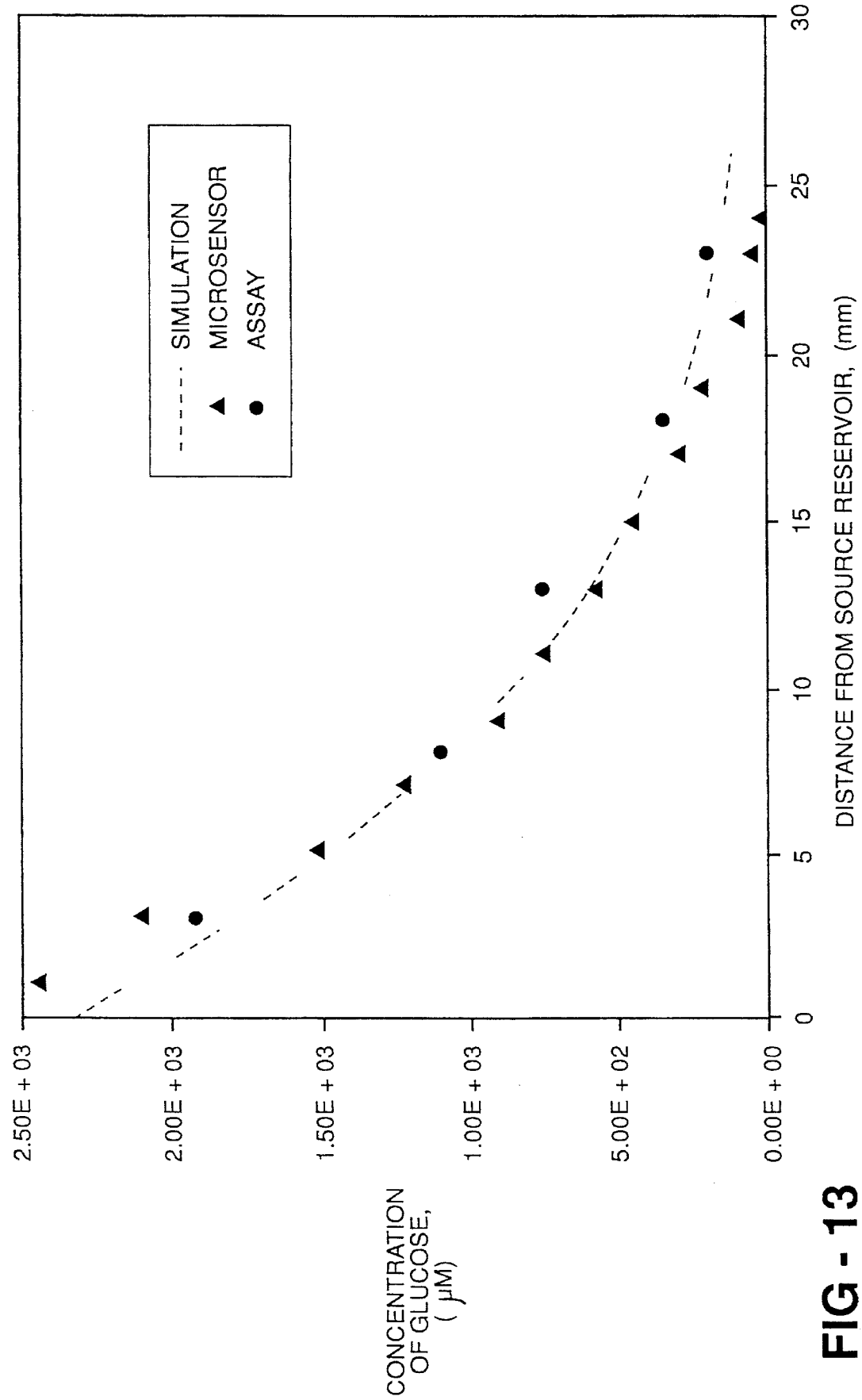
FIG. 13 shows glucose gradient along the central axial line of the diffusion gradient chamber as measured with the microbiosensor of the present invention; and compared with an enzyme assay and model simulation data.

EXAMPLE 7—Measuring Concentration Gradients Inside a Diffusion Gradient Chamber Several glucose microbiosensors have been successfully tested for measuring concentration gradients of soft-solid gels inside a Diffusion Gradient Chamber. The Diffusion Gradient Chamber (DGC) houses a slab-shaped layer of semi-solid agarose gel. Liquid reservoirs on opposite sides of the chamber allow chemical gradients to be established across the gel. The DGC has been shown to be useful in studying microbial chemotaxis (e.g. bacterial movement in presence of a chemical concentration gradient as attractant or repellent) and isolating microorganisms having novel properties [Emerson et al., 1994]. The experimental protocol was the following:

(i) Prepare the DGC and establish a glucose concentration gradient.
(ii) Calibrate the microbiosensor in the calibration chamber (outside the DGC) as described above.
(iii) Mount the microbiosensor in the micromanipulator arm. The micromanipulator arm with the sensor will move in the horizontal plane, along the X axis and the Y axis of the rectangular DGC arena.
(iv) The glucose concentration can be recorded as picoammmeter current output in any point (X, Y) by lowering the microbiosensor in to the agarose gel with the micromanipulator arm.
(v) After mapping the whole DGC arena, the microbiosensor amperage data are converted into glucose concentrations using the calibration curve and plotted (FIG. 12).
(vi) To validate the microsensor data, a number of samples have been extracted from the gel, and the glucose concentration was measured using the standard enzymatic assay from Sigma Chemical Co. An example of the microbiosensor data vs. both the standard assay and predictions of a mathematical model is showed in FIG. 13.

EXAMPLE 8

Figure 11A:
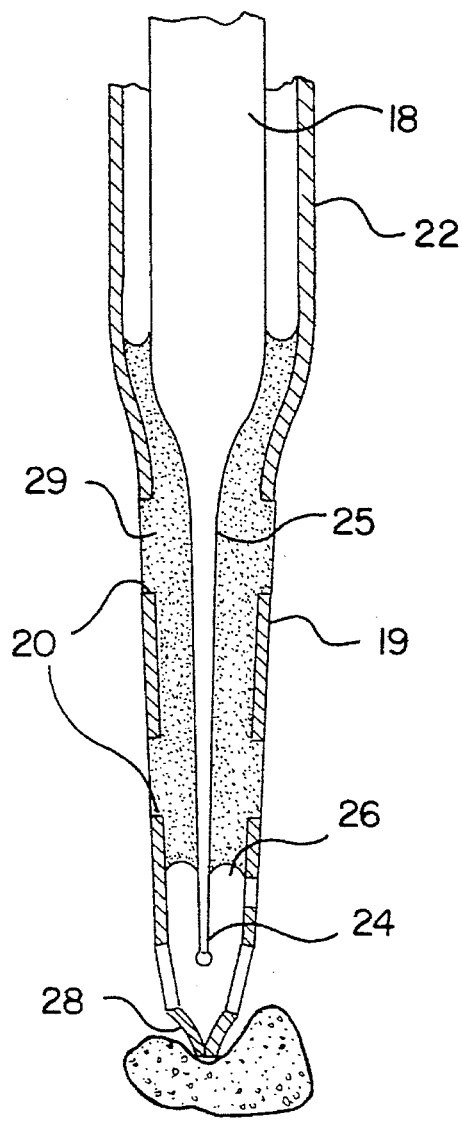
FIGS. 11a and 11b show the needle-type microbiosensor of the present invention in two additional alternative embodiments (a,b)
Figure 11B:
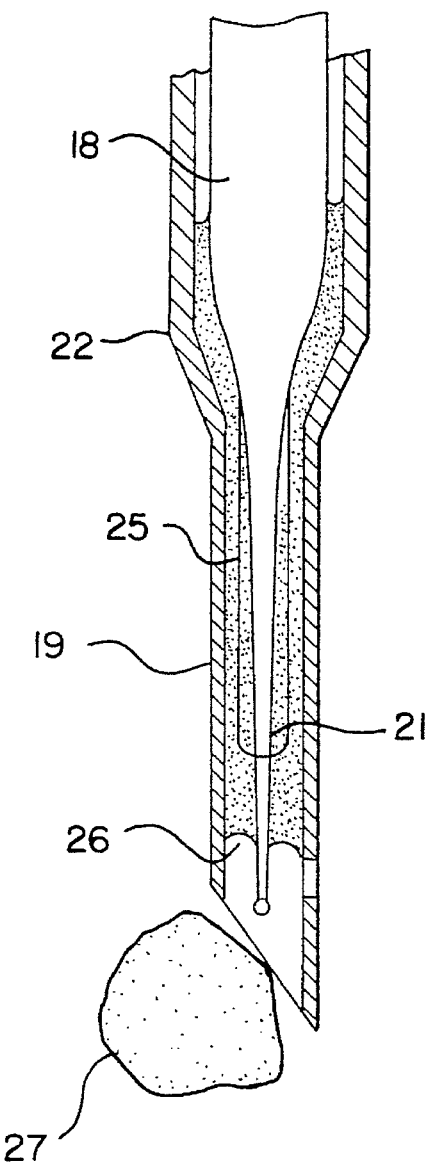

An alternative embodiment of the present invention as shown in FIG. 11 is utilized in the present Example. A protective sheath was placed about the microbiosensor. The protective sheath preferably is non-toxic, bio-compatible and resilient, that is, break resistant. The protective sheath can be austenitic, stainless steel (AISI 304, AISI 304L or AISI 316). Another example is an austenitic alloy with molybdenum, providing better corrosion resistance, AISI 316 or AISI 316L.

The two different types of needle designs shown in FIG. 11a, b are suitable for specimens having different textures:

(a) a closed end, with tapered tip edge and lateral holes on the cylindro-conical hollow stem, for harder textures with less liquid content.

(b) an open end, cylindrical 60 deg. cut tip edge and lateral slit on cylindrical hollow stem, for softer textures with more liquid content. In all cases, the total area of openings in the needle's wall measure less than 7854 µm², equivalent to a single circular opening in the protective sheath of diameter less than 100 µm, or a square slit in the wall measuring 88 µm×88 µm, or two circular openings having 70 µm diameter each.

By using a precision tool, the stainless steel needle's wall 19 is drilled (20) or cut longitudinally (21), deburred and sanded so that the microbiosensor tip can be seen and tracked under the microscope, while safely advanced inside the specially designed needle 22. This is done while the microsensor cylindrical case 23 is mounted in the micromanipulator, having the needle mounted on the microscope stage.

When the sensing tip 24 can be seen as occupying the best possible position inside the needle, a 10 ml syringe is used to inject epoxy (available from Devcon Corp., Wood Dale, Ill. or Super Glue Corp., Hollis, N.Y.) resin in a thin, continuous layer between the needle wall and the cylindro-conical, microsensor glass outer case 25. Care must be taken that the resin, when cured, is close enough to the electrode tip to protect it from external particulate objects, yet still leave it access to the surrounding medium for measuring solute concentration.

The result is the needle-type microbiosensor. The delicate glass tip is slightly recessed into a small resin cavity 26 inside the needle hollow body, and therefore is well protected from encountering objects. Particles 27 massive enough to possibly break the glass tip should be too large to penetrate the holes or "windows" of the needle and will thus slide past along the tapered surface of stainless steel 28 and or cured resin 29.

EXAMPLE 9—Influence of Temperature on Microbiosensor Measurements

Figure 14A:
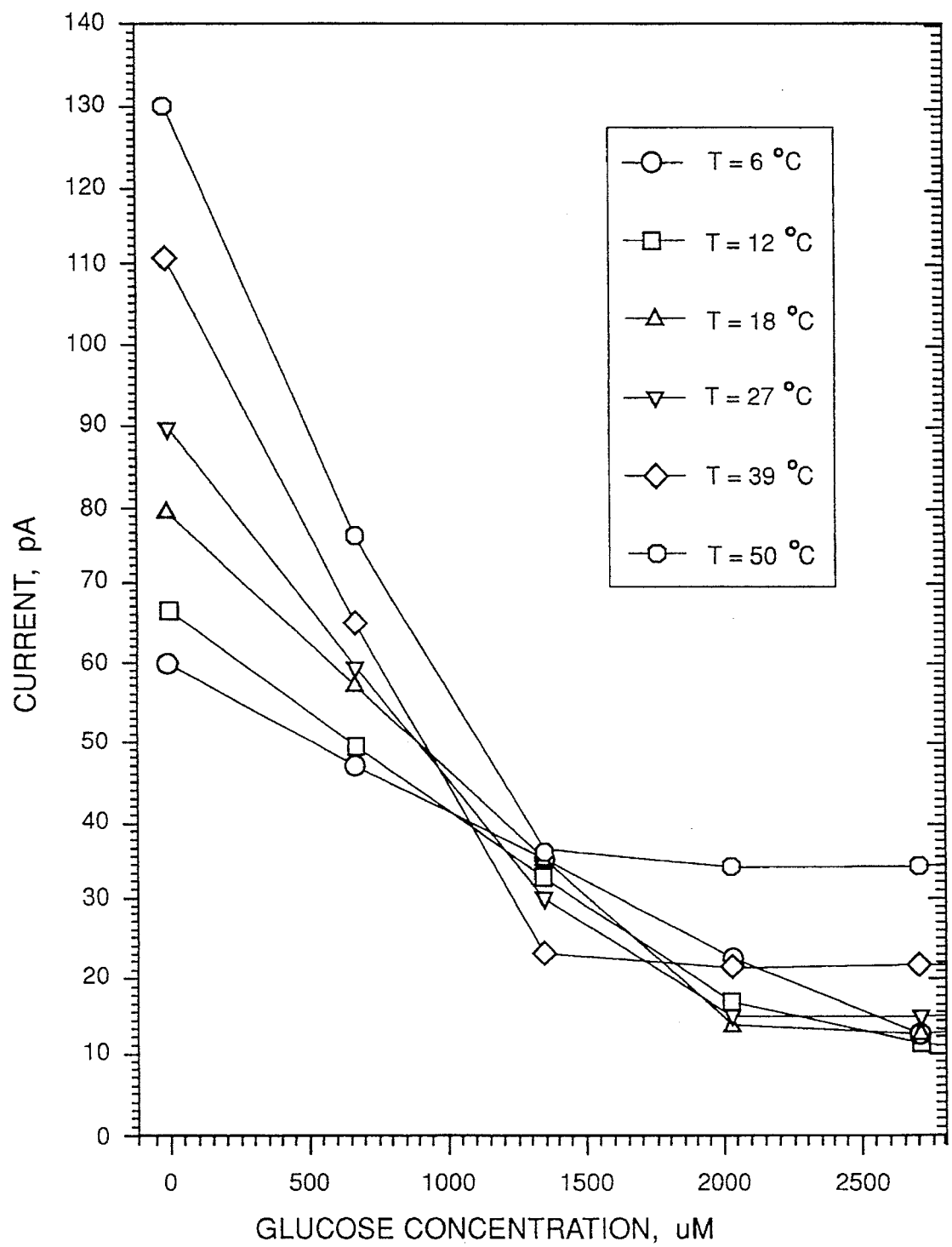
FIGS. 14a and 14b show the temperature effect on glucose calibration for two microbiosensors of the present invention.
Figure 14B:
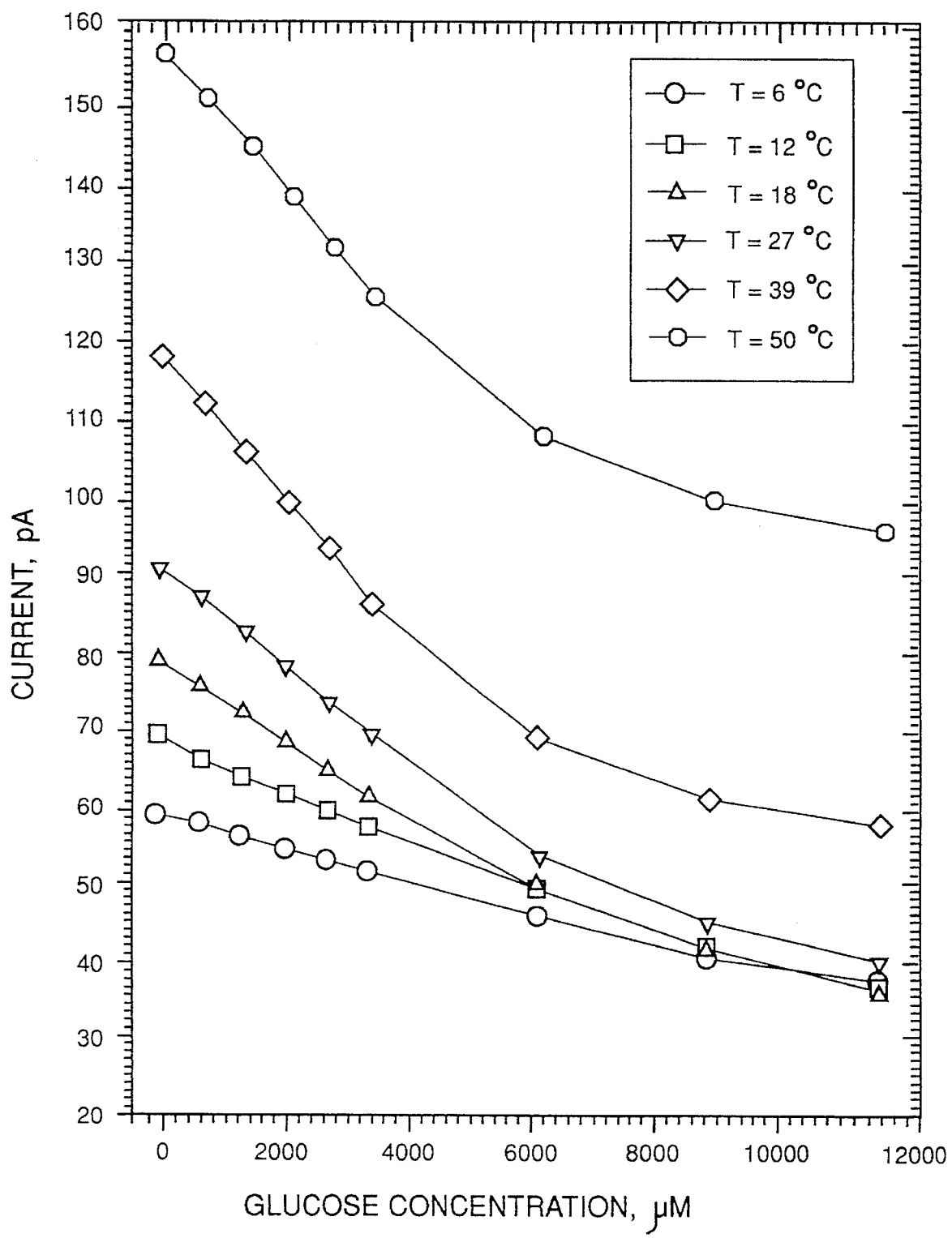

We examined the effect of temperature on the performance of two glucose microbiosensors in the range of 5 to 50° C. Calibrations tests were conducted with the calibration chamber. The buffer was maintained with the temperature preset with ±0.2° C. accuracy, by immersion in a thermostated bath. Then the usual calibration procedure was repeated for several temperatures (6°, 12°, 18°, 27°, 39° and 50° C.). The results are shown in FIG. 14 *a,b*.

EXAMPLE 10—Arrhenius Plot

Figure 15:
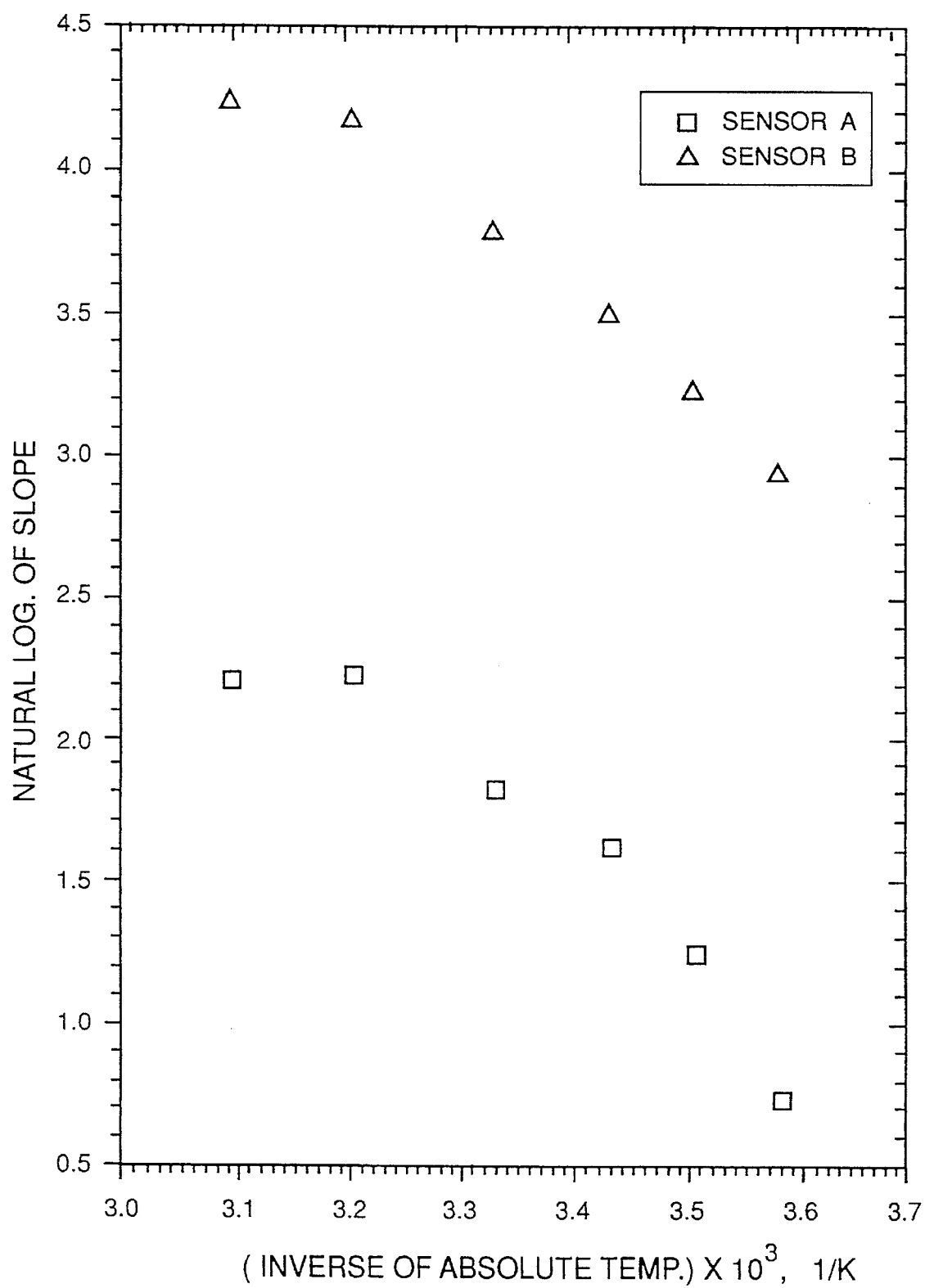
FIG. 15 shows an Arrhenius plot for the data shown in FIGS. 14a and 14b.

If the Arrhenius equation is used [e.g. Zeffren and Hall, 1973], the same microbiosensor data can be plotted as the natural log of the sensitivity versus the inverse of the absolute temperature, as in FIG. 15. The activity of the immobilized glucose oxidase can be calculated from the slope of the linear segment of the curve, e.g. for microbiosensor B the apparent activity is 33 kJ/mol, compared to 29–50 kJ/mol from other authors [Sakura & Buck, 1992; Cass et al., 1984]. The difference in microbiosensor sensitivity results from different glucose oxidase loadings. The optimal temperature is shown to be around 39° C.

EXAMPLE 11—Short-term, wet-storage (STWS) 72 hours operational life span

Each geometric symbol represents a calibration test done with the microbiosensor.

Figure 16:
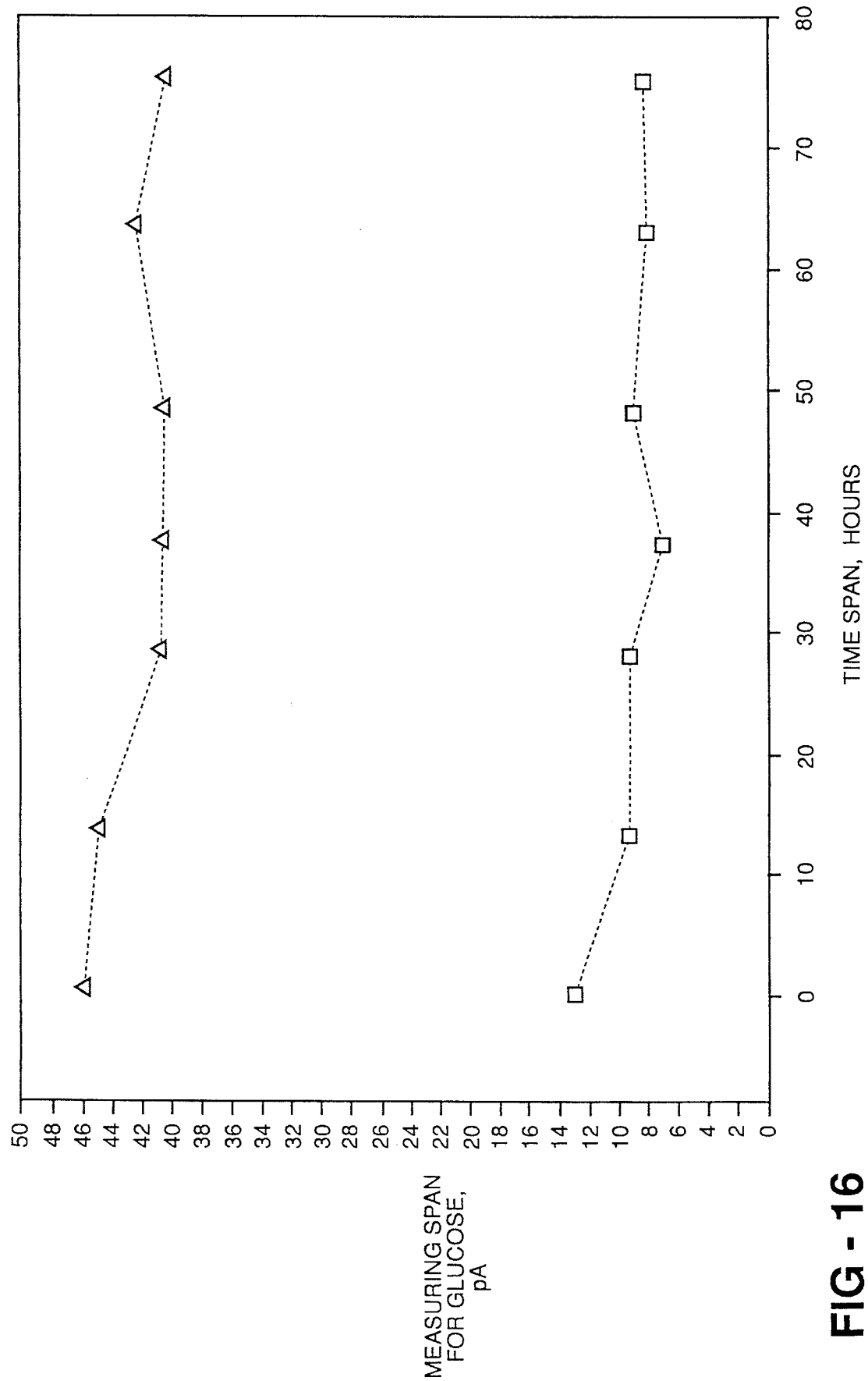
FIG. 16 shows a short term, wet storage (72 hours) stability test for glucose calibration using two microbiosensors of the present invention.

The stability and reproducibility of the microbiosensor were measured during short-term, wet-storage (STWS) continuous monitoring. Calibration tests were performed at 10–12 hour intervals for a total of minimum 72 hours. The microbiosensors were stored between calibrations at room temperature, with the tip immersed 4 mm in phosphate buffer, in an open glass beaker, with no stirring. The results are shown in the FIG. 16.

EXAMPLE 12—Long-term, dry storage (LTDS) operational life span

Figure 17:
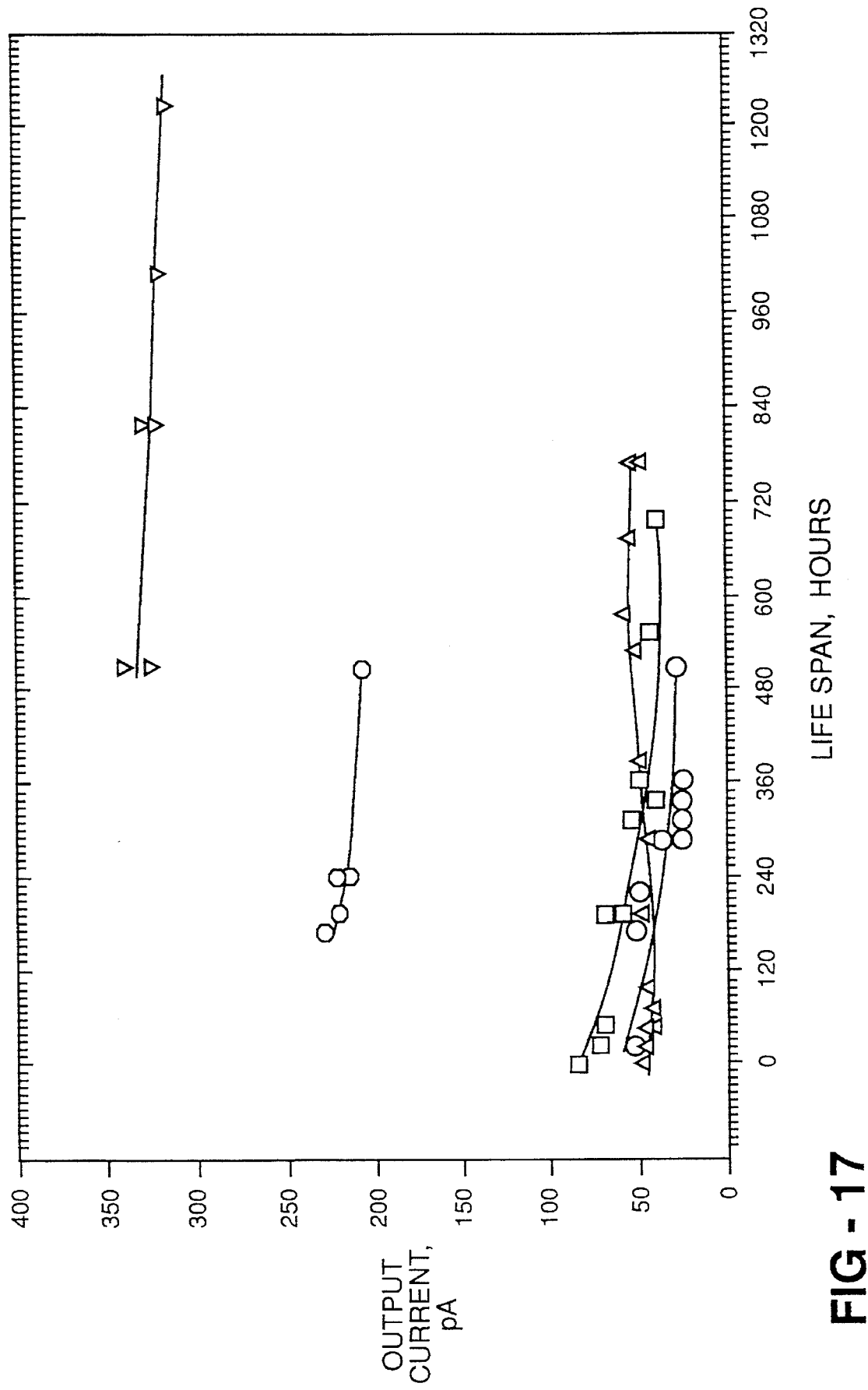
FIG. 17 shows the results of a long term, dry storage stability test; plotted is dissolved oxygen measuring range vs. life span for several microbiosensors of the present invention.
Figure 18:
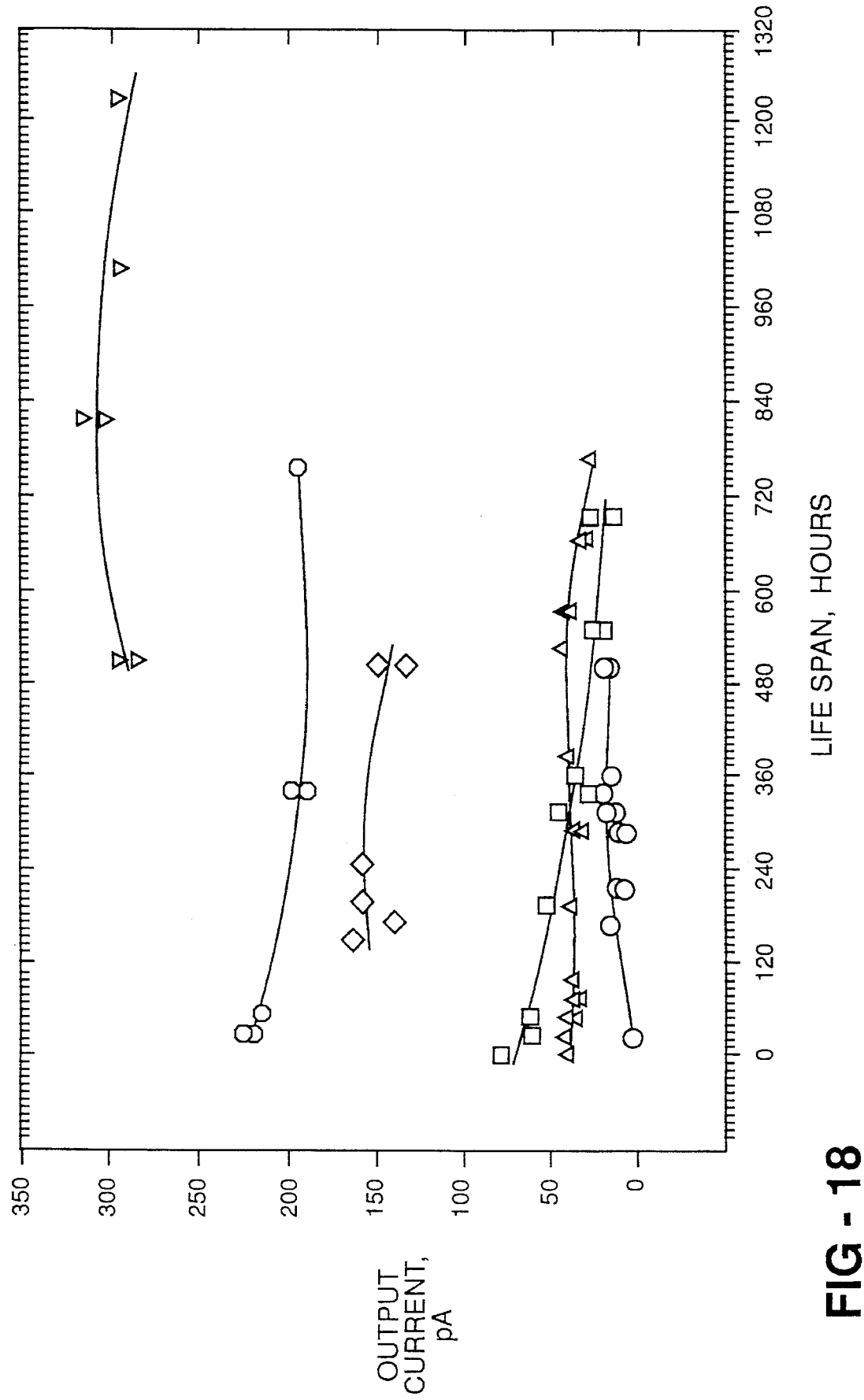
FIG. 18 shows the results of a long term, dry storage stability test; plotted is an analyte measuring range vs. life span for several microbiosensors of the present invention.
Figure 19:
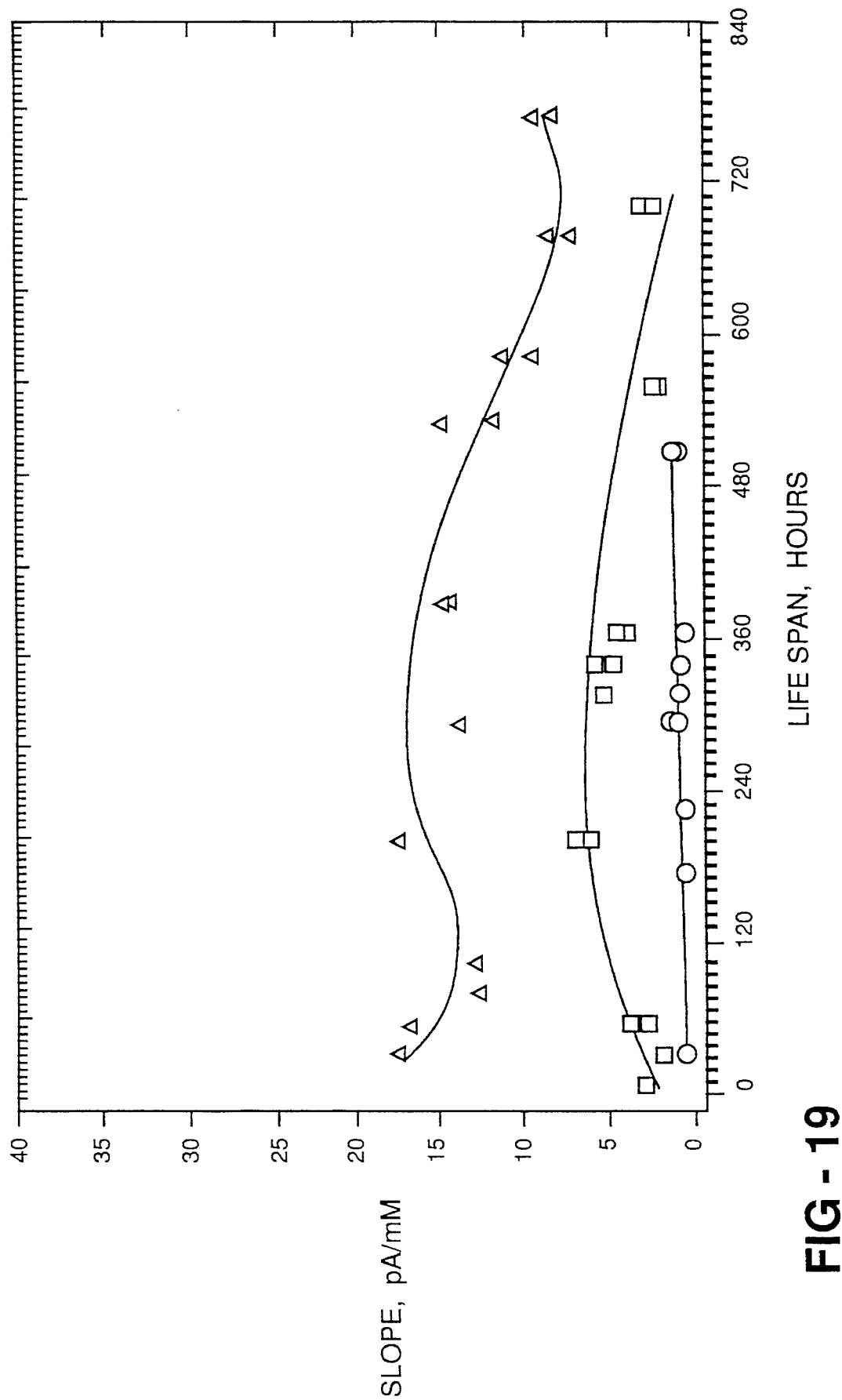
FIG. 19 shows the results of a long term, dry storage stability test; plotted is analyte measuring sensitivity vs. life span for several microbiosensors of the present invention.

Microbiosensors encased in a protective sheath was mounted in a flexible holder and immersed with the tip (the first 4 mm) in an open glass beaker containing buffered distilled water, with the thermostat at 22°±1° C. and uniformly stirred at 80 rpm with a magnetic bar. The test consisted of (i) calibration by immersion in buffer subsequently saturated with dissolved air and nitrogen and (ii) calibration by adding analyte controlled aliquots, as described previously. To examine stability and reproducibility during the LTDS-discontinuous monitoring, the oxygen measuring range [pA], analyte measuring range [pA], and analyte measuring sensitivity [pA/mM] were assessed over the whole life span. Between tests, the microbiosensors were stored dry, inside glass tubes with silica gel powder at 4° C. The results are shown in the FIGS. 17, 18 and 19. Each geometric symbol represents a calibration test done with the microbiosensor.

EXAMPLE 13—The effect of the polymer outer protective membrane

Figure 20A:
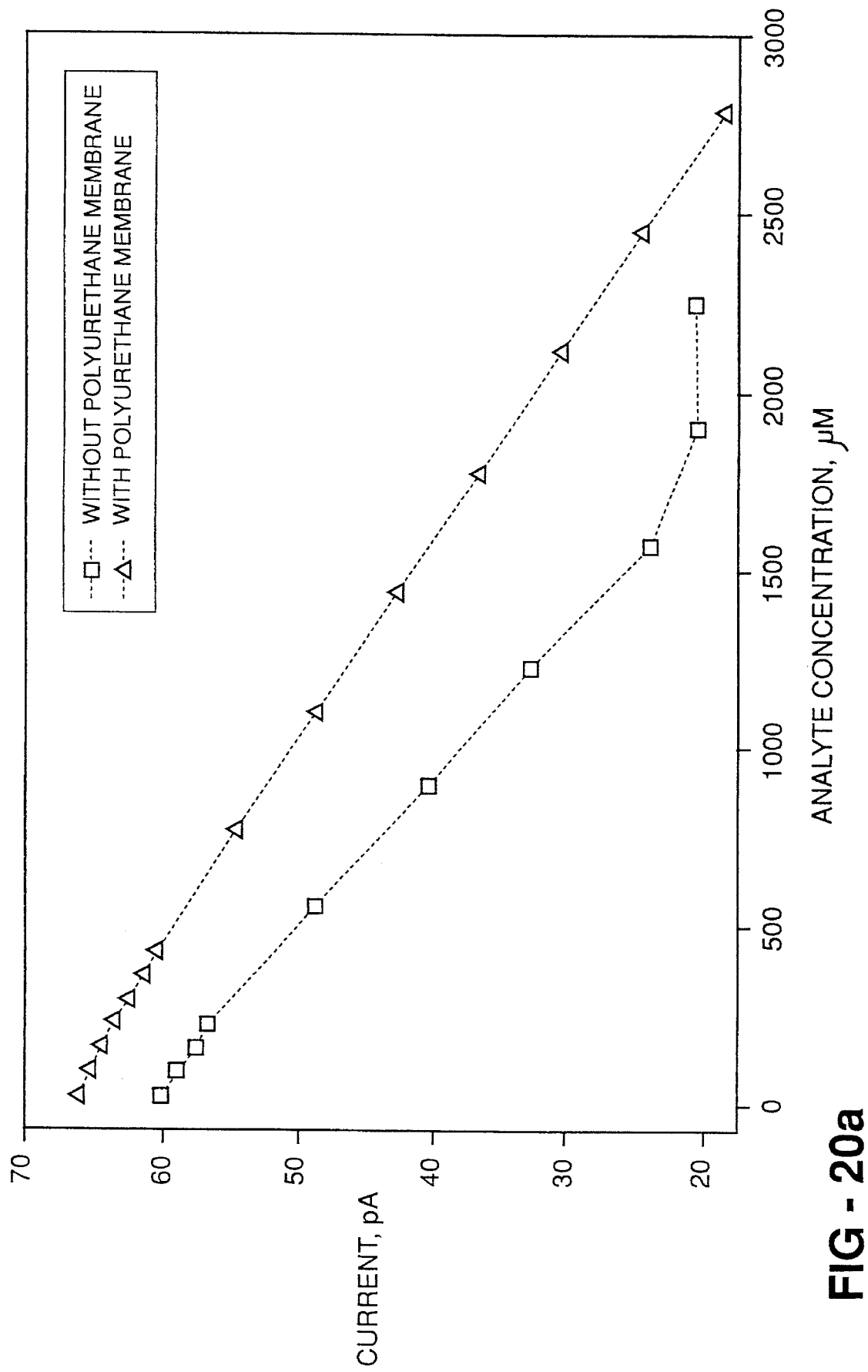
FIGS. 20a and 20b show the effect of the protective membrane on measuring range for two microbiosensors of the present invention.
Figure 20B:
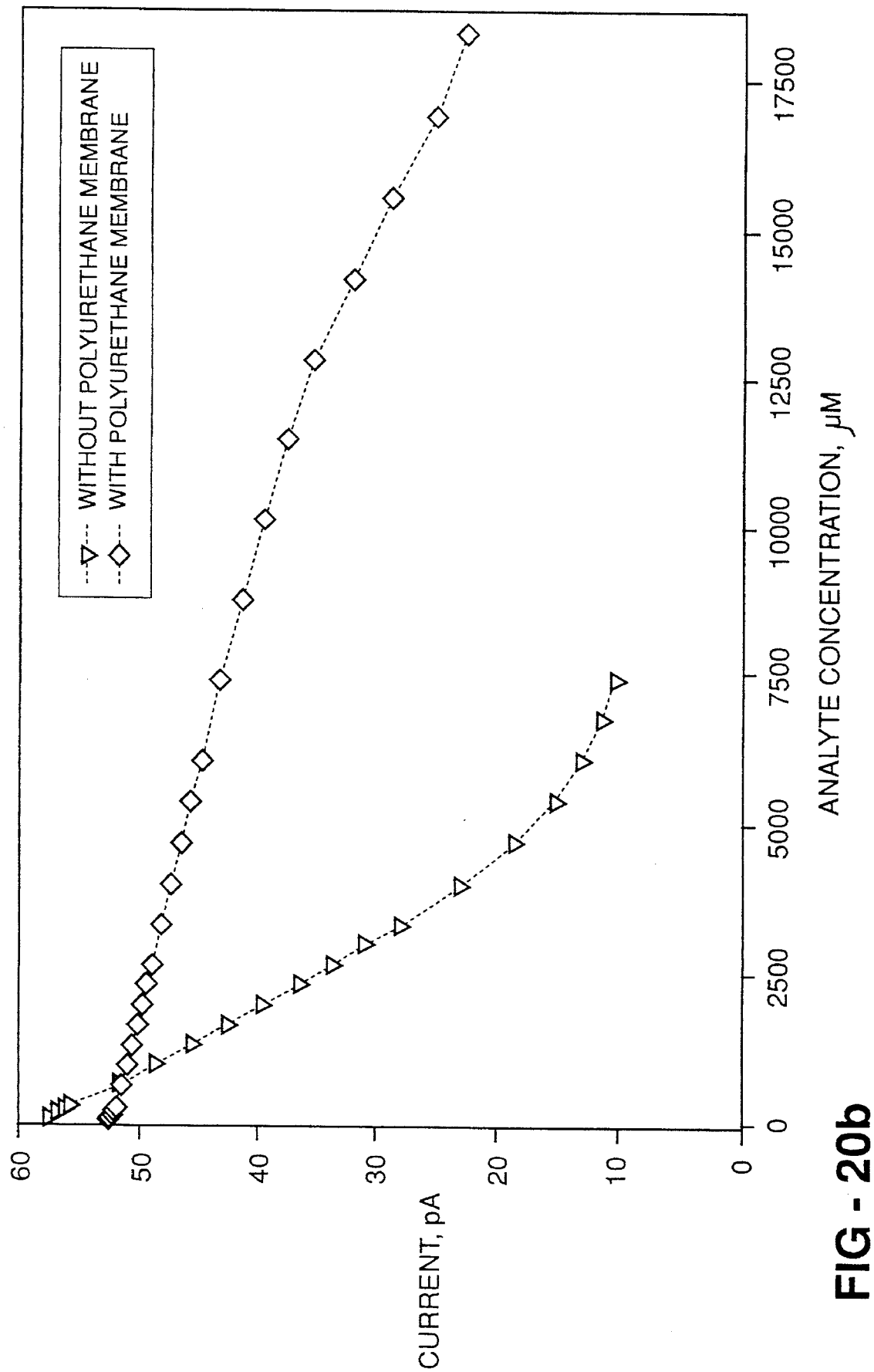

The effect of the polymer outer protective membrane on the analyte measuring range is shown in FIG. 20 *a,b*. A thin 2–3 µm polyurethane membrane appears to double the measuring span, and the use of a thick 6–7 µm membrane widens the measuring range three times.

EXAMPLE 14—Linear measuring ranges of microbiosensors

Figure 6:
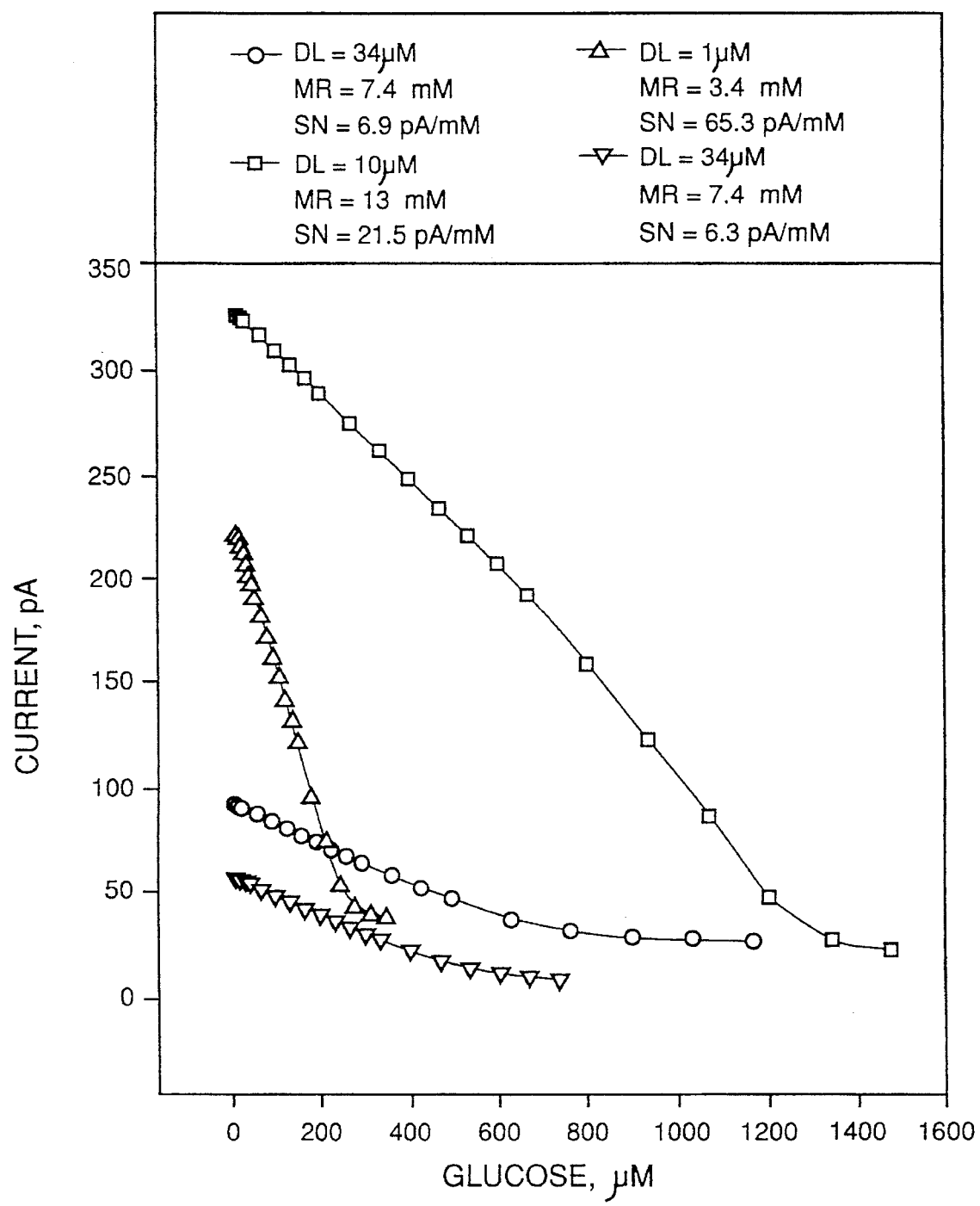
FIG. 6 shows the characteristics of several glucose microbiosensors of the present invention.

Typical features of glucose microbiosensor are shown in FIG. 6.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

For example, the present invention has utility in a wide variety of applications including food toxicology, crop and food quality assessment, probing immobilized biocatalysts, biofilms, and measuring the activity of large single cells.

Some general features of the microbiosensors of the present invention are shown below in Table 1.

TABLE 1

| Analyte | Immobilized Enzyme | Detection Limit | Response Time | Linear Range |
| --- | --- | --- | --- | --- |
| Glucose | Glucose Oxidase | 1–10 µM | 0.4–0.8 sec. | 0–10 mM |
| Galactose | Glucose Oxidase | 1–10 µM | 0.5–1.5 sec. | 0–7 mM |
| Lactose | β-galactosidase | 500 µM | 1–2 sec. | 0.5–400 mM |
| Choline | Choline Oxidase | 5–15 µM | 1–2 sec. | 0–10 mM |
| $H_2O_2$ | Catalase | 1–10 µM | 1 sec. | 0–2.5 mM |

REFERENCES

Akasaka, S. & K. Yamamoto (1994) *Mol. Gen. Genet.*, 243(5): 500–505.

Alvarez-Icaza M., Bilitewski U. (1993) *Analytical Chemistry*, 65(11): 525 A.

Besedina E. I. and Grin N. V. (1987) *Gigiena i. Sanitariya* (Russian) 19: 79.

Cass, A. E. G. et al. (1994) *Analytical Chemistry* 56(4): 667–671.

Clark, L., Jr. (1970) U.S. Pat. No. 3,535,455. *Membrane-PolarographicElectrode System and Method with Electrochemical compensation.*

Duncan C. J. (1989) *Virchows Archiv Abteilung B.* (German) *Cell Pathology* 56(4): 271.

Durand-Cavagna et al. (1989) *Fundamental and Applied Toxicology,* 13(3): 500.

Emerson D., Worden M. and Breznak J. A. (1994) *Applied and Environmental Microbiology,* April 1994, p. 1269.

Gropper S. S. et al. (1993) *Journal of the American Diet Association,* 93: 328.

Guilbaullt, G. G. (1984) *Analytical uses of immobilized enzymes,* Marcel Dekker, Inc., New York.

Hayatsu H. (1991) *Mutagens in Food, Detection and Prevention,* CRC Press.

Karube I. et al. (1993) *Biosensors & Bioelectronics,* 8(3–4): 219.

Karube I. and Suzuki M. (1990) *Biosensors*, Oxford University Press, New York, p. 155.

Karube I. and Nakanishi K. (1994) *IEEE Engineering in Medicine and Biology*, June/July, p. 364.

Kierstan, M. P. J. & M. P. Coughlan (1985) *Immobilization of Cells and Enzymes by Gel Entrapment*, Ch. 3 in "Immobilized cells and enzymes. A practical approach", J. Woodward Ed., IRL Press, Oxford Kierstan, M. P. J. & M. P. Coughlan (1991) *Immobilization of Proteins by noncovalent procedures: principles and applications*, Ch. 2 in "Protein Immobilization", R. F. Taylor Ed., Marcel Dekker, Inc., New York Kress-Rogers E. et al. (1992) *Nestle Meeting on Biosensors, Opportunities for the Food Industry*, Lausanne, Switzerland, p. 41.

Lai C. S. et al. (1987) *Biophysical Journal* 52(4): 625.

Larsson R. et al. (1986) *Chemico-Biological Interactions*, 60 (3): 317.

Lee S. et al. (1992) *Biosensors & Bioelectronics*, 60(3): 317.

Luong et al. (1991) *Biosensors & Bioelectronics*, 6: 547.

Martins, E. A. & R. Meneghini (1994) *Biochem. J.*, 299(1): 137–140.

Milner J. (1992) *Diet and Carcinogenesis, Food Safety Assessment, ACS Symposium Series* 484, Chapter 27.

Milton et al. (1990) *American Revue of Respiration Diseases*, 142(1): 84.

Nakagawa Y. and Moldeus P. (1992) *Biochemical Pharmacology*, 44(6): 1059.

Neun D. J. et al. (1992) *Archieves of Toxicology* (Berlin), 66(1): 11.

O'Connor J. (1992) *Australian Journal of Nutrition and Diet*, 49(3): 87.

Peteu, S. F., Emerson, D. & R. M. Worden (1995) *Amperometric Microbiosensors for Food Testing*, presentation for American Chemical Society National Meeting, August, Chicago Ill.

Planck et al. (1987) *Polyurethanes in Biomedical Engineering*, Elsevier, New York.

Revsbech N. P. (1989) *Limnology and Oceanography*, 34: 474.

Risphon J. et al. (1993) U.S. Pat. No. 5,147,781, assigned to Weizmann Institute, Rehovot, Israel.

Sakura, S. & R. P. Buck (1992) *Bioelectrochemistry and Bioenergetics*, 343(28): 387–400.

Scheller F. (1993) *Applied Microbiology and Biotechnology*, 38: 556.

Simmons D. M., Kearney J. N. (1993) *Biotechnology and Applied Biochemistry*, 17(1): 23.

T. Abe, Y. Y. Lau and A. G. Ewing (1992) *Analytical Chemistry*, 64: 2160–2163.

Taylor S. L. et al. (1992) *"Food Allergies"*, in *Food Safety Assessment, ACS Symposium Series* 484, Maple Press, York, Pa., Chapter 28.

Trevors J. T. and Basaraba J. (1980), *Bulletin of Environmental Contamination and Toxicology*, 25(4): 672.

Woodward, J. (1985) *Immobilized cells and enzymes. A practical approach*, IRL Press Oxford.

Y. T. Kim, D. M. Scarnulis and A. G. Ewing (1986) *Analytical Chemistry*, 58: 1782–1786.

What is claimed is:

1. A microbiosensor that is an amperometric, internal referenced, oxygen microelectrode measuring device, having a biological interface as a sensing device that consumes or generates oxygen when exposed to an organic analyte in a response directly proportional to the tapered concentration of the analyte comprising:

a tapered casing having an aperture at its tip no greater than 40 micrometers, enclosed within the tapered casing an anode, which serves as an internal reference; a cathode; an electrolyte therebetween and a membrane in the aperture that prevents contact between a specimen and the components inside the tapered casing, and attached to the tip an immobilized biological interface layer which measures an analyte.

2. The microbiosensor of claim 1, wherein the biological interface layer contains an enzyme that consumes or generates oxygen in a dose-dependent response in the presence of an organic analyte.

3. The microbiosensor of claim 1, wherein the biological interface layer consists of a mixture of enzymes that act in concert to consume or produce oxygen in a dose-dependent response in the presence of an organic analyte.

4. The microbiosensor of claim 1, wherein the biological interface layer is comprised of immobilized microbial cells that consume oxygen in a dose-dependent response in the presence of an organic analyte.

5. The microbiosensor of claim 1, wherein the biological interface layer which selectively measures a specific analyte or organic compound in a mixture of organic compounds.

6. The microbiosensor of claim 1, wherein the enzyme is selected from the group consisting of an enzyme and mixture of enzymes, which detects glucose, lactose, fructose, sucrose, galactose, choline, hydrogen peroxide, toluene, benzene, benzoates, alkanes of 1 to 4 carbon atoms, ammonia and mixtures thereof.

7. The microbiosensor of claim 2, wherein the layers that lie between the cathode and a sample to be tested are sufficiently thin and permeable to the analyte to allow a response time of the microbioprocessor of less than 5 seconds.

8. The microbiosensor of claim 1, wherein the diameter of the tip is sufficiently small, and the current output is sufficiently low to give a spatial measuring resolution as low as 30 micrometers.

9. The microbiosensor of claim 1, wherein a enzyme, enzymes or cells are immobilized in a layer of polymeric material.

10. The microbiosensor of claim 1, wherein the immobilized enzyme, enzymes or cell layer is coated with a chemically inert protective membrane.

11. A cylindroconical-type microbiosensor comprising:

a tapered casing having an aperture at its tip of no greater than 4 micrometers;

enclosed within the tapered casing an anode, which serves as an internal reference; a cathode; an electrolyte therebetween, and a membrane in the aperture that prevents contact between the specimen and the components inside the tapered casing, and attached to the tip an immobilized biological interface layer no greater than 25 micrometers in diameter which measures an analyte, and the tip being enclosed within a sheath.

12. The cylindroconical-type microbiosensor of claim 11, wherein the sheath is adhesively secured to the casing.

13. The microbiosensor of claim 11, wherein a protective sheath is designed to allow insertion of a prefabricated microbiosensor into it at a defined distance from the bottom of the sheath.

14. The microbiosensor of claim 13, wherein the openings in the protective sheath have a surface area less than 8000 square micrometers, equivalent to a single opening less than 100 micrometers in diameter, or equivalent to two circular openings having 70 micrometers each, or a square slit measuring 88 micrometers×88 micrometers.

15. The microbiosensor of claim 11, wherein a bottom of a protective sheath is open to allow free passage of the analyte.

* * * * *